United States Patent [19]

Holland

[11] 4,138,399

[45] Feb. 6, 1979

[54] SULFAMYLBENZOIC ACID

[75] Inventor: Gerald F. Holland, Old Lyme, Conn.

[73] Assignee: Pfizer Inc., New York, N.Y.

[21] Appl. No.: 802,498

[22] Filed: Jun. 1, 1977

Related U.S. Application Data

[60] Division of Ser. No. 713,412, Aug. 11, 1976, which is a division of Ser. No. 481,195, Jun. 20, 1974, Pat. No. 3,992,441, which is a division of Ser. No. 318,213, Dec. 26, 1972, Pat. No. 3,843,662, which is a continuation-in-part of Ser. No. 206,514, Dec. 9, 1970, abandoned, which is a continuation-in-part of Ser. No. 72,156, Sep. 14, 1970, abandoned.

[51] Int. Cl.$^2$ ............................................ C07D 295/16
[52] U.S. Cl. .............................. 260/239.8; 260/239.6; 260/239.65; 260/239.7

[58] Field of Search ............ 260/239.6, 239.65, 239.7, 260/239.8; 424/229

[56] References Cited

U.S. PATENT DOCUMENTS

| | | | |
|---|---|---|---|
| 2,910,488 | 10/1959 | Novello | 260/397.7 |
| 3,346,568 | 10/1967 | Schmidt et al. | 260/239.8 |
| 3,444,177 | 5/1969 | Schmidt et al. | 260/239.7 |
| 3,565,920 | 2/1971 | Werner | 260/347.2 |
| 3,879,402 | 4/1975 | Holland | 260/293.73 |

*Primary Examiner*—John D. Randolph
*Attorney, Agent, or Firm*—Connolly and Hutz

[57] ABSTRACT

Certain mono- and disubstituted-5-sulfamylbenzoic acids, many of which are novel, and their use in lowering blood lipid levels in mammals.

14 Claims, No Drawings

SULFAMYLBENZOIC ACID

CROSS-REFERENCE TO RELATED APPLICATIONS

This application is a division of application Ser. No. 713,412 filed Aug. 11, 1976 which is a division of application Ser. No. 481,195 filed June 20, 1974 now U.S. Pat. No. 3,992,441 which is a division of application Ser. No. 318,213 filed Dec. 26, 1972 now U.S. Pat. No. 3,843,662 which is a continuation-in-part of application Ser. No. 206,514 filed Dec. 9, 1971 and now abandoned which is a continuation-in-part of application Ser. No. 72,156 filed Sept. 14, 1970 and now abandoned.

BACKGROUND OF THE INVENTION

Atherosclerosis, a form of arteriosclerosis, is characterized by accumulation of lipids in the aorta and in the coronary, cerebral and peripheral arteries of the lower extremities. As these masses increase in size, the risk of thrombosis and occlusion arises.

It has been found that those suffering from the disease exhibit elevated levels of plasma lipoprotein, of which cholesterol and triglycerides comprise major constituents. While the etiology of the disease is not yet fully understood, it is believed that β-lipoproteins play an important role, and it has been recommended that dietary habits which promote low β-lipoprotein plasma levels be observed. In addition, various therapeutic agents such as estrogens, thyroxine analogs and sitosterol preparations have been used to lower plasma cholesterol levels in individuals prone to the condition.

It has now been found that certain mono- and disubstituted-5-sulfamylbenzoic acids are effective in reducing plasma lipid levels. These compounds can be expected to be useful in the treatment of atherosclerosis and related cardiovascular diseases associated with elevated lipid levels.

A number of 5-sulfamylbenzoic acids are found in the literature:

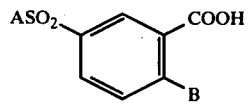

| A | B | Reference |
|---|---|---|
| $NH_2$ | Cl | (1) |
| $CH_3NH$ | Cl | (2) |
| $(CH_3)_2N$ | Cl | (2) |
| $C_2H_5NH$ | Cl | (2) |
| $(CH_3)(C_2H_5)N$ | Cl | (2) |
| $(C_2H_5)_2N$ | Cl | (2) |
| $i-C_3H_7NH$ | Cl | (2) |
| $(CH_3)(i-C_3H_7)N$ | Cl | (2) |
| $NH_2$ | Br | (3) |
| $(CH_3)NH$ | Br | (3) |
| $(CH_3)_2N$ | Br | (3) |
| $(C_2H_5)_2N$ | Br | (3) |
| | Br | (3) |
| $CH_2(CH_2)_3-N$ | | |
| $(CH_3)NH$ | $NH_2$ | (2) |
| $(C_2H_5)NH$ | $NH_2$ | (2) |
| $(C_2H_5)_2N$ | $NH_2$ | (2) |
| $(CH_3)(C_2H_5)N$ | $NH_2$ | (2) |
| $(i-C_3H_7)NH$ | $NH_2$ | (2) |
| $(CH)(i-C_3H_7)N$ | $NH_2$ | (2) |
| | $NH_2$ | (4) |
| $CH_2(CH_2)_4-N$ | | |
| $(CH_3)_2N$ | $C_2H_5NH$ | (2) |
| $(CH_3)_2N$ | $(i-C_3H_7)NH$ | (2) |

| A | B | Reference |
|---|---|---|
| $(CH_3)_2N$ | $C_4H_9NH$ | (2) |

(1) Jackman, et al., J. Pharm. Pharmacol., page 679 (1962)
(2) Belgian Patent 620,741 (1963), (Chem. Abstr., 59, 11359)
(3) Kunzle, et al., Helvetica Chimica Acta, 52, 625 (1969)
(4) U.S. Pat. 2,453,104 (1948), (Chem. Abstr., 43, 7710)

In addition, 4-sulfamylbenzoic acids are found in the literature:

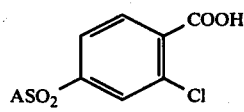

| A | Reference |
|---|---|
| $(C_3H_7)_2N$ | (5) |
| $(i-C_3H_7)_2N$ | (5) |
| $(C_4H_9)_2N$ | (5) |
| $C_6H_5CH_2NH$ | (5) |
| | (5) |
| $CH_2(CH_2)_4-N$ | |

(5) British Patent 795,937 (1958) (Chem. Abstr., 53, 297)

A series of sulfamylbenzoic acids with utility as uricosuric agents for rheumatism and arthritis are claimed in West German patent application DT No. 2,109,339. None of the 5-sulfamyl compounds of the present invention, however, demonstrated uricosuric activity when tested.

Although the foregoing summary has been disclosed by a diligent search of the literature, it does not, of course, purport to be an exhaustive listing of all known sulfamylbenzoic acids. Nevertheless, so far as can be determined, the ability of the 5-sulfamylbenzoic acids of the present invention to reduce plasma lipid levels has never before been recognized.

SUMMARY OF THE INVENTION

It has been discovered that blood lipid levels may be reduced by administering to a hyperlipemic mammal a substance selected from 5-sulfamylbenzoic acids and the amides, lower alkyl esters and salts thereof with pharmacologically acceptable bases, said substances being substituted in the 2-position by hydrogen, chloro, fluoro, bromo, hydroxy, methoxy, methylthio, amino, mono- and di-lower-alkyl amino, benzylamino, phenethylamino, piperidino, mono- and di-lower-alkyl-piperidino, pyrrolidino, hexamethyleneimino or morpholino, and in the 3-, 4- or 6-position by hydrogen, fluoro, chloro, bromo, methoxy, trifluoromethyl or methyl, with the proviso that if the 2-substituent is hydrogen the substituent at the 3-, 4- or 6-position is selected from the group consisting of fluoro, chloro, bromo, methoxy, methyl and trifluoromethyl.

Also considered within the scope of the present invention are congeners wherein the 2-positional substituent is trifluoromethyl, lower alkoxy or lower alkyl.

The hypocholesteremic activity appears to be shared by all these mono- and disubstituted 5-sulfamylbenzoic acids, but one would obviously avoid any substituents known to be toxic at a level required for lipid-lowering effectiveness.

One preferred class of compounds of the aforementioned configuration is that wherein the sulfamyl group is piperidinosulfonyl or substituted piperidinosulfonyl having up to two substituents each selected from the group consisting of alkyl, alkyloxy and alkyloxyalkyl of one to four carbon atoms in each alkyl group, hydroxy, chloro, bromo, trifluoromethyl, phenyl, tolyl, benzyl, benzyloxy, benzyloxymethyl, chloromethyl and hydroxymethyl.

A second preferred class of compounds is that wherein the sulfamyl group is RR'NSO$_2$-, wherein R and R' together with the nitrogen to which they are attached form a heterocyclic ring selected from the group consisting of morpholino, thiomorpholino, piperazinyl, hexamethyleneimino, heptamethyleneimino, octamethyleneimino, 3-azabicyclo[3,2,2]nonanyl, tetrahydroisoquinolyl, tetrahydropyridyl and mono- and disubstituted derivatives of said heterocyclic rings . . . said substituents being selected from the group consisting of alkyl, alkyloxy and alkyloxyalkyl of one to four carbon atoms in each alkyl group, hydroxy, chloro, bromo, trifluoromethyl, phenyl, tolyl, benzyl, benzyloxy, chloromethyl and hydroxymethyl.

A third preferred class of compounds is that wherein the sulfamyl group is

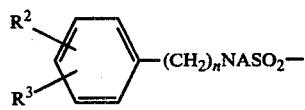

wherein
n has a value from 0 to 3;

A is selected from the group consisting of hydrogen, lower alkyl, cycloalkyl of 5 to 8 carbon atoms, benzyl and phenyl; and R$^2$ and R$^3$ are each selected from the group consisting of hydrogen, chloro, bromo, alkyl and alkoxy of from one to four carbon atoms, carboxy, trifluoromethyl, phenyl, benzyl and benzyloxy.

A fourth preferred class of compounds is that wherein the sulfamyl group is R$^4$R$^5$NSO$_2$— wherein R$^4$ is hydrogen or lower alkyl and R$^5$ is lower alkyl or cycloalkyl of 5 to 8 carbon atoms.

As discussed below, many of the substances of the aforementioned classes are novel, and as such form part of the present invention.

DETAILED DESCRIPTION OF THE INVENTION

One subclass of novel and particularly preferred compounds of the present invention embraces those of the formula:

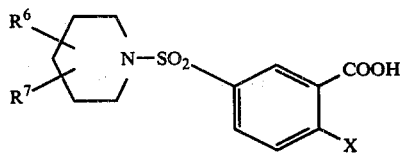

wherein
X is selected from the group consisting of fluoro, chloro, bromo, piperidino, mono- and di-lower-alkylpiperidino, hexamethyleneimino and morpholino;

R$^6$ is selected from the group consisting of alkyl, alkyloxy and alkyloxyalkyl of one to four carbon atoms in each alkyl group, hydroxy, chloro, bromo, trifluoromethyl, methylene, oxo, phenyl, tolyl, benzyl, benzyloxy, benzyloxymethyl, chloromethyl and hydroxymethyl; and R$^7$ is selected from the group consisting of hydrogen, alkyl, alkyloxy and alkyloxyalkyl of one to four carbon atoms in each alkyl group, hydroxy, chloro, bromo, trifluoromethyl, phenyl, tolyl, benzyl, benzyloxy, benzyloxymethyl, chloromethyl and hydroxymethyl.

Especially preferred are the compounds of the latter structure wherein X is fluoro, chloro or bromo and R$^6$ and R$^7$ are each lower alkyl or benzyl.

A second and related subclass of novel and particularly preferred compounds of the present invention embraces those of the formula:

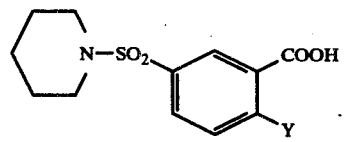

wherein Y is selected from the group consisting of piperidino and mono- and di-lower-alkyl piperidino.

A third subclass of novel and particularly preferred compounds of the present invention embraces those of the formula:

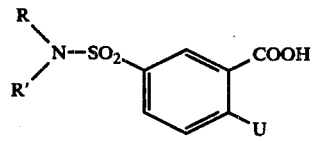

wherein
U is selected from the group consisting of fluoro, chloro, bromo, di-lower-alkylamino, piperidino, mono- and di-lower-alkylpiperidino, morpholino, and hexamethyleneimino;

and R and R' together with the nitrogen to which they are attached form a heterocyclic ring selected from the group consisting of morpholino, thiomorpholino, piperazinyl, hexamethyleneimino, heptamethyleneimino, octamethyleneimino, 3-azabicyclo[3,2,2-]nonanyl, tetrahydroisoquinolyl, tetrahydropyridyl and mono- and disubstituted derivatives of said heterocyclic rings;

said substituents being selected from the group consisting of alkyl, alkyloxy and alkyloxyalkyl of one to four carbon atoms in each alkyl group, hydroxy, chloro, bromo, trifluoromethyl, phenyl, tolyl, benzyl, benzyloxy, chloromethyl and hydroxymethyl.

A fourth subclass of novel and particularly preferred compounds of the present invention embraces those of the formula:

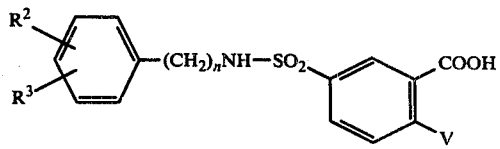

wherein n has a value from 0 to 3;

V is selected from the group consisting of fluoro, chloro, bromo, piperidino and mono- and di-lower-alkylpiperidino; and $R^2$ and $R^3$ are each selected from the group consisting of hydrogen, chloro, bromo, alkyl and alkoxy of from one to four carbon atoms, carboxy, trifluoromethyl, phenyl, benzyl and benzyloxy.

A fifth and closely related subclass of novel and particularly preferred compounds of the present invention embraces those of the formula:

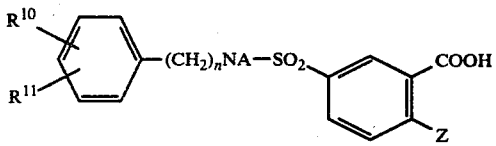

wherein n has a value from 0 to 3;

A is selected from the group consisting of lower alkyl, cycloalkyl of 5 to 8 carbon atoms, benzyl and phenyl;

Z is fluoro, chloro or bromo; and $R^{10}$ and $R^{11}$ are each selected from the group consisting of hydrogen, lower alkyl, chloro, bromo and phenyl.

A sixth subclass of novel and particularly preferred compounds of the present invention embraces those of the formula:

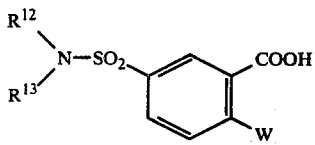

wherein W is selected from the group consisting of fluoro, chloro, bromo, piperidino and mono- and di-lower-alkylpiperidino; $R^{12}$ is hydrogen or lower alkyl; and $R^{13}$ is cycloalkyl of 5 to 8 carbon atoms.

A seventh and closely related subclass of novel and particularly preferred compounds of the present invention embraces those of the formula:

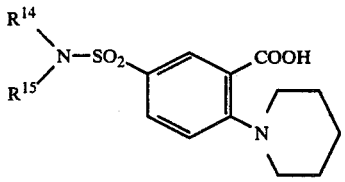

wherein $R^{14}$ and $R^{15}$ are each lower alkyl.

An eighth subclass of preferred compounds of the present invention are represented by the formula:

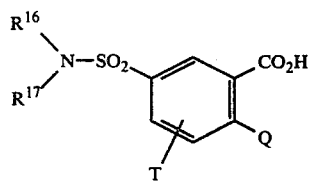

wherein Q is selected from the group consisting of hydrogen, chloro, fluoro, bromo, methoxy, methyl, di-lower-alkylamino, piperidino and hexamethyleneimino; T is selected from the group consisting of chloro, fluoro, bromo, methyl, methoxy and trifluoromethyl; $R^{16}$ is selected from the group consisting of hydrogen and lower alkyl; $R^{17}$ is selected from the group consisting of lower alkyl and phenylalkylene of the formula:

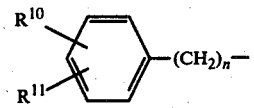

wherein n has a value of 0 to 3 and $R^{10}$ and $R^{11}$ are each selected from the group consisting of hydrogen, methyl, chloro, bromo and phenyl; and $R^{16}$ and $R^{17}$ when considered together with the nitrogen to which they are attached form a heterocyclic ring selected from the group consisting of morpholino, piperidino, mono- and dimethylpiperidino and hexamethyleneimino.

The sulfamylbenzoic acids of the present invention have been found to be well tolerated in the form of the free carboxylic acid. If desired, however, they may be administered in the form of an amide, lower alkyl ester or salt of a pharmacologically acceptable base.

The amides include not only the unsubstituted amides but amides of pharmacologically acceptable amines, for example, the amino acids, such as glycine or 4-aminobutyric acid. The amides are readily prepared by standard techniques, for example, by treating a corresponding sulfamylbenzoic acid ester in alcohol with ammonia, or by combining the corresponding sulfamyl benzoyl chloride with amine under basic conditions and precipitating the amide product with mineral acid.

Of the lower alkyl esters, the ethyl ester will generally be preferred. In addition, esters of complex alcohols such as acetamidoethyl alcohol may be employed. The esters may be employed. The esters may be prepared by condensation of the acid with the corresponding alcohol in the presence of acid catalyst.

The pharmacologically acceptable salts include the ammonium, sodium, potassium, calcium and magnesium salts, as well as salts with pharmacologically acceptable amines. The salts are prepared by conventional procedures, for example, by adding the acid to an aqueous solution containing an equivalent amount of the appropriate base, followed by concentration to obtain the desired product. Although salts formed from pharmacologically-unacceptable bases are not useful therapeutically, they may be used in the purification. For example, an impure acid can be purified by dissolving it in an aqueous solution containing a pharmacologically-unacceptable base and extracting the resulting salt solution with organic solvent to remove non-acidic impurities. The free, purified acid is then isolated by acidifying the aqueous solution and filtering.

Although parenteral modes of administration of the compounds of the present invention may be employed, oral administration is effective and preferred for its obvious convenience. The products of the invention are tested in vivo for hypolipemic activity in rats. Groups, each comprising 4 animals, of normal Sprague-Dawley (Charles River) male rats weighing from 160 to 220 grams are fed rat chow containing the compound under test for two overnight feeding periods. On the morning of the third day the animals are anesthetized and bled from the abdominal aorta. The total plasma cholesterol is then determined by the method of J. J. Carr and I. J.

Drekter, reported in *Clin. Chem.*, 2, 353 (1956). Most of the tests are conducted at a feed concentration of 0.15 to 0.25 weight percent of the compound under test, but lower levels, 0.01 to 0.10 weight percent, are employed in some instances where particularly high potency is anticipated. The plasma cholesterol level of the treated animals is found to be significantly reduced when compared to animals not receiving the test compound.

This pharmacological test for measuring hypocholesteremic activity is a reasonably reliable indication that similar activity in humans can be expected. In fact, those compounds effective in the rat which have been tested in humans have demonstrated similar activity. p-Chlorophenoxyisobutyric acid, ethyl ester, marketed as Atromid-S, a well-known and clinically effective hypocholesteremic agent, causes a 30–35% cholesterol fall in the rat test when administered at a level of 0.25% in the feed.

In humans, an individual having a plasma cholesterol level above 260 mg. percent (mg. per 100 ml.) or a plasma triglyceride level about 150 mg. percent is regarded as hyperlipemic. The term "lipids" is used herein in the broad sense to include triglycerides, cholesterol, phospholipids and free fatty acids. Plasma lipids are carried in the body in the form of lipoproteins, i.e., protein complexes. These may be separated by electrophoresis into several fractions: high density or α-lipoprotein, containing a high proportion of phospholipids; low-density or β-lipoprotein, containing a major proportion of cholesterol; very low-density or pre-β-lipoprotein; and chylomicrons; the latter two fractions containing a major proportion of triglycerides. In a particular individual, one of the four fractions may be elevated. The agents of the present invention depress plasma lipoprotein, with associated cholesterol and triglyceride, and hence are expected to be of value in hyperlipoproteinemic individuals.

One of the novel compounds of the present invention, 2-chloro-5-(cis-3,5-dimethylpiperidinosulfonyl)benzoic acid, which exhibits higher potency than Atromid-S in the rat test, has produced significant depression in plasma cholesterol and triglycerides in human studies. Overall reductions compare closely with those produced by Atromid-S in similar populations. In these clinical studies, the compound was administered in three equally divided doses at daily levels of 0.5–1.5 grams. It is now being further evaluated in hyperlipemic humans in the form of capsules containing 250 mg. of active ingredient, at a dosage schedule of two capsules three times daily. Further testing at a level of one capsule three times daily, equivalent to 0.75 gram per day, is also planned.

Among those compounds of the preferred classes, 2-chloro-5-(cis-3,5-dimethethylpiperidinosulfonyl)benzoic acid, 2,3-dichloro-5-(cis-3,5-dimethylpiperidinosulfonyl)benzoic acid, 2-chloro-5-(N-ethyl-N-[2-p-chlorophenethyl]-aminosulfonyl)benzoic acid and 2,3-dichloro-5-(N-ethyl-N-[2-p-chlorophenethyl]-aminosulfonyl)benzoic acid are particularly outstanding.

Obviously, the optimum dosage level for a particular compound of the present invention will vary with the relative potency of the substance and with the age, weight and response of the particular patient. An approximation of suitable dosage levels for various compounds can be estimated from their potency in the rat test relative to a standard which has been tested in humans, such as Astromid-S or 2-chloro-5-(cis-3,5-dimethylpiperidinosulfonyl)benzoic acid. In determining relative potency, dose response curves are preferably constructed by rat testing at several dosage levels, for example, at seven levels. A compound which proves twice as potent as the standard in this test will generally be evaluated in toxicology as a candidate for use at half the level employed with the standard.

Having full regard for the foregoing factors, it is considered that an effective daily dosage of the compounds of the present invention in humans will generally range from about 0.3 to 3 grams per day, in single or divided dosage, or at about 5 to 50 mg. per kg. of body weight. These values are illustrative, and there may, of course, be individual cases where higher or lower dosage ranges are merited.

The sulfamylbenzoic acids of this invention can be administered either alone, or preferably, in combination with a pharmaceutically-acceptable carrier. They may be combined with various pharmaceutically-acceptable, inert carriers in the form of tablets, capsules, lozenges, troches, powders, aqueous suspensions or solutions, elixirs, syrups and the like. Suitable carriers include solid liluents or aqueous media and non-toxic organic solvents. The oral pharmaceutical compositions of this invention may be suitably sweetened and flavored by means of various agents commonly employed for such a purpose.

For parenteral administration, solutions or suspensions of the herein described sulfamylbenzoic acids in sesame or peanut oil or in aqueous propylene glycol solutions can be employed, as well as sterile aqueous solutions of the corresponding water-soluble salts. Such solutions are suitable for intramuscular and subcutaneous administration. Sterile aqueous solutions are additionally useful for intravenous injection, provided that their pH is suitably adjusted and buffered, if necessary, and the liquid diluent rendered isotonic with saline or glucose.

The herein disclosed compounds may also be useful in other aspects of abnormal metabolism, the latter possibly accounting for clinical problems in diabetes, pancreatitis, coronary heart disease, and cerebrovascular disease. Hence the ability of sulfamylbenzoic acids of this invention to regulate lipid metalbolism might find utility in the treatment of said diseases.

The compounds of the invention are readily prepared by reactions well known to those skilled in the art, as summarized in the reaction schemes of Charts 1 and 2, wherein I → II represents chorosulfonation of a 2-substituted benzoic acid, where X is fluoro, chloro, bromo or methyl and T is hydrogen, fluoro, chloro, bromo, trifluoromethyl, methoxy or methyl;

II → III represents reaction of a 2-substituted-5-chlorosulfonyl benzoic acid with amine in the presence of alkali or in a non-aqueous medium such as methylene chloride;

III → IV represents replacement of a 2-halo substituent by a 2-amino group, effected by refluxing the sulfamylbenzoic acid with the corresponding amine;

III → V represents replacement of a 2-halo substituent by a 2-alkoxy group, effected by heating the sulfamylbenzoic acid with the corresponding alcohol in the presence of sodium hydride;

III → VI represents replacement of a 2-halo substituent by a methylthio group, effected by heating the sulfamylbenzoic acid with sodium or potassium salt of methylmercaptan;

III → VII represents replacement of a 2-halo substituent by a 2-hydroxyl group, effected by heating the sulfamylbenzoic acid in the presence of strong alkali such as sodium hydroxide or potassium hydroxide;

IX → X represents chlorosulfonation of a substituted benzoic acid, where T is a substituent at the 3- or 4-position selected from the group consisting of fluoro, chloro, bromo, trifluoromethyl, methyl and methoxy;

X → XI represents reaction of a substituted-5-chlorosulfonylbenzoic acid with an amine in the presence of alkali or in a non-aqueous medium such as methylene chloride;

XII → XIII represents a series of reactions converting a 5-nitro-6-substituted benzoic acid (or lower alkyl ester) where T is fluoro, chloro, bromo, methyl, methoxy or trifluoromethyl to the corresponding 5-sulfamyl-6-substituted benzoic acid via reduction of the nitro group employing stannous chloride followed by diazotization of the amino moiety and reaction of the resulting diazonium salt with sulphur dioxide to form the sulfonyl chloride, which is subsequently reacted with an appropriate amine in the presence of alkali or in a non-aqueous medium such as methylene chloride; and XIV → XV represents N-alkylation of a substituted-5-phenyl- or -phenylalkyl-aminosulfonyl benzoic acid, e.g., by treatment with the corresponding alkyl or aralkyl halide or dialkyl sulfate in the presence of aqueous alkali, wherein Q, $R^{10}$, $R^{11}$, A, T and n are as previously defined.

The following examples illustrate in greater detail the preparation of typical members of the compounds of the invention.

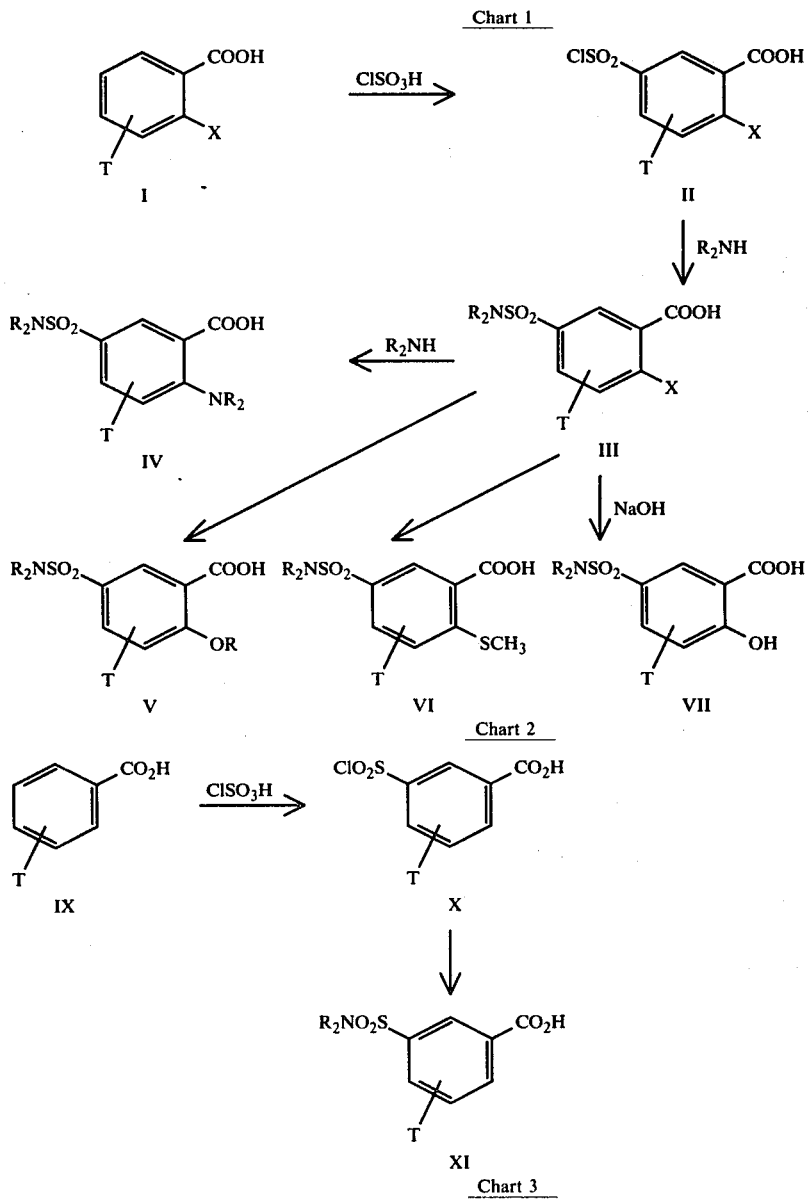

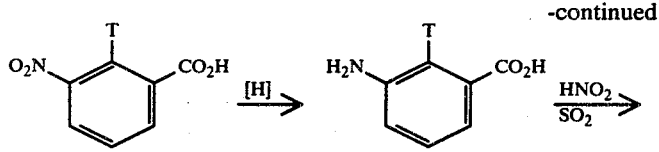

-continued

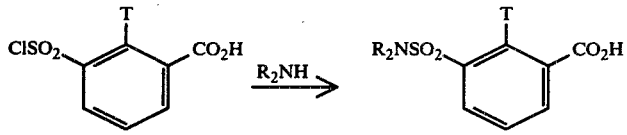

Chart 4

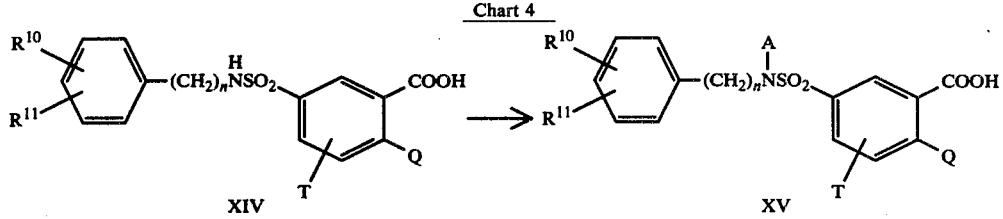

The requisite starting materials leading to the products of the present invention are commercial reagents, or are compounds whose syntheses are either described previously in the chemical literature or are prepared by chemical reactions well known to those skilled in the art.

EXAMPLE 1

2-Chloro-5-chlorosulfonylbenzoic Acid

A mixture of o-chlorobenzoic acid (2.0 kg.) and chlorosulfonic acid (10.5 kg.) is heated at 99°–100° C. for 5 hours. The reaction mixture is cooled to 25° C. and then slowly poured into a 10 liter mixture of ice and water. The addition requires about 1 hour, and the temperature is maintained below 10° C. during this period by the addition of more ice. The final volume of slurry after the quench is about 40 liters. The solid material is collected and thoroughly washed on the funnel with fresh water. The crude wet cake is dissolved in 16 liters of diethyl ether. The ether layer is washed once with 2 liters of saturated aqueous sodium chloride solution and then dried over anhydrous magnesium sulfate. The filtered ether solution is concentrated in vacuo with the continual addition of hexane. The resulting hexane slurry is concentrated to a final volume of approximately 8 liters and filtered. The crystalline cake is washed with hexane and dried in the atmosphere to give 2.5 kg. of product (76.8% of theory), m.p. 149°–151° C.

cis-3,5-Dimethylpiperidine Hydrochloride 3,5-Lutidine (6475.0 g.) is hydrogenated under 1000 psi hydrogen pressure in ethanol using 1665 g. of 5% rhodium on carbon catalyst (50% $H_2O$) at room temperature. The catalyst is filtered off and anhydrous hydrogen chloride bubbled into the filtrate at a temperature below 40° C. until the solution is strongly acidic. The solution is then concentrated in vacuo to a thick slurry which is diluted with 40 liters of hexane. The crystalline material is filtered off and dried in the atmosphere to give 8.9 kg. of crude product. The crude 3,5-dimethylpiperidine hydrochloride is dissolved in 14 liters of water and the pH of this solution adjusted to 7.0 with dilute sodium hydroxide solution. The mixture is washed with 7 l. and then with 3 l. of chloroform to remove unreduced 3,5-lutidine. The aqueous solution is then adjusted to pH 12–13 by the addition of 40% sodium hydroxide solution and extracted with 6 l. and then with 3 l. of chloroform. The combined chloroform extract is dried over anhydrous magnesium sulfate and chilled to 5° C. in an ice bath. Anhydrous hydrogen chloride is then injected until the solution is strongly acidic. The chloroform solution is concentrated in vacuo as benzene is continuously added. When most of the chloroform has been replaced, the product is filtered from about 36 l. of benzene. The filter cake is washed with cold benzene and hexane, and air dried, to obtain 4.8 kg. of product, m.p. 222°–224° C.

2-Chloro-5-(cis-3,5-dimethylpiperidinosulfonyl)benzoic Acid

2-Chloro-5-chlorosulfonylbenzoic acid (510.2 g.) and cis-3,5-dimethylpiperidine hydrochloride are slurried in 7.0 l. of water and stirred at 15° C. as a cold solution of 240.0 g. of sodium hydroxide in 6 l. of water is added in a steady stream. The hazy reaction mixture is stirred at 20°–25° C. for 1 hour and then filtered by suction through a funnel precoated with diatomaceous earth filter aid. The filtrate is acidified with concentrated hydrochloric acid and the resulting precipitate collected. The cake is washed with methanol and ether, and air-dried to obtain 650.0 g. of crude product. This is dissolved in 6 l. of 1:1 isopropyl alcohol:chloroform and filtered. The filtrate is concentrated in vacuo to about 3 l. and the crystalline material filtered off. The filter cake is washed with isopropyl alcohol and ether. Air drying gives 471.0 g. of crystalline product, m.p. 250°–251° C.

Anal. Calc'd for $C_{14}H_{18}O_4NSCl$: C, 50.67; H, 5.47; N, 4.22. Found: C, 50.73; H, 5.46; N, 4.24.

In the same way, 2-chloro-4-(cis-3,5-dimethylpiperidinosulfonyl)benzoic acid, m.p. 233°–234° C., is prepared from 2-chloro-4-chlorosulfonylbenzoic acid.

EXAMPLE 2

2-Chloro-5-(trans-dl-3,5-dimethylpiperidinosulfonyl)-benzoic Acid

The mother liquors of the reduced 3,5-lutidine of Example 1 are evaporated to dryness. The residue contains approximately 78% trans and 22% cis isomers. A portion of this material is reacted with 2-chloro-5-chlorosulfonylbenzoic acid by the method of Example 1. Recrystallization from methylene chloride replaced with benzene yields the desired product, m.p. 188°–191.5° C.

EXAMPLE 3

2-Chloro-5-($\beta,\beta'$-dichloro-diethylaminosulfonyl)benzoic Acid

To a solution of 1.8 gram (10 m moles) of $\beta,\beta'$-dichlorodiethylamine hydrochloride in 20 ml. water, 20 ml. acetone and 30 ml. 1N aqueous sodium hydroxide is added 2.55 gram (10 m moles) of 2-chloro-5-chlorosulfonyl benzoic acid. After stirring at room temperature for one hour, the mixture is washed with 20 ml. ether and acidified with concentrated hydrochloric acid to obtain 0.7 gram crystalline product, m.p. 161°–163° C. Recrystallization from benzenehexane does not change the melting point.

Anal. Calc'd for $C_{11}H_{12}O_4NSCl_3$ (MW 360.65): C, 36.64; H, 3.35; N, 3.88. Found: C, 36.66; H, 3.39; N, 3.71.

EXAMPLE 4

2-Chloro-5-(4-Chloropiperidinosulfonyl)benzoic Acid

4-Chloropiperidine hydrochloride is prepared by refluxing 4-hydroxypiperidine hydrochloride, 4.2 g., with 20 ml. thionyl chloride for 10 minutes, and evaporating to dryness.

10 m moles of this product is permitted to react with 10 m moles of 2-chloro-5-chlorosulfonyl benzoic acid as described in the previous example. After washing with ether and acidifying, the reaction mixture is extracted with ethyl acetate and the extract is evaporated to dryness. The residue is then dissolved in a mixture of 3 ml. acetone and 10 ml. ethyl acetate and passed over 30 grams silica gel packed in a column in a solution of 5% acetic acid in 1:1 benzene:hexane. The column is eluted with the same solvent mixture and the product isolated by evaporation of first effluent fractions. The residue is purified by dissolving in 20 ml. acetone, adding an equal volume of hexane, and decanting the supernatant from the resulting precipitate. The supernatant is then concentrated to half volume to crystallize 0.45 gram of product, m.p. 193°–195° C.

Anal. Calc'd for $C_{12}H_{13}O_4NSCl_2$ (MW 338.2): C, 42.62; H, 3.87; N, 4.14. Found: C, 42.79; H, 3.99; N, 3.91.

EXAMPLE 5

2-Chloro-5-(2-[p-chlorophenyl]ethylaminosulfonyl)-benzoic Acid

2-Chloro-5-chlorosulfonyl benzoic acid, 3.5 g. (0.014 mole), is added to a solution of 2-(p-chlorophenyl)ethylamine, 6.5 g. (0.042 mole) in 25 ml. methylene chloride. The resulting slurry is stirred overnight and filtered to recover 9.7 g. of residue. This is recrystallised three times from aqueous isopropanol, then dissolved in 1N aqueous sodium hydroxide, washed three times with ether, and then acidified with conc. hydrochloric acid. The resulting precipitate is recrystallized twice from aqueous isopropanol to yield the desired product, m.p. 176°–178° C.

Anal. Calc'd for $C_{15}H_{13}O_4NSCl_2$: C, 48.14; H, 3.50; N, 3.72. Found: C, 48.19; H, 3.31; N, 3.42.

EXAMPLE 6

2-Chloro-5-chlorosulfonylbenzoic acid is reacted by the method of Example 1 with each of the indicated amines to yield the corresponding sulfamylbenzoic acid.

| Amine | Product, m.p. (° C.) |
|---|---|
| 2,5-dimethylpiperidine | 128.5–131 |
| 3,5-dimethylmorpholine | 201–208 |
| 3-piperidylcarbinol | 191–193 |
| 3,5-diethylpiperidine | 182–184 |
| 2,2-dimethylthiomorpholine | 181.5–183 |
| 2-benzylpiperidine | 164–166 |
| 4-ethoxy-4-phenylpiperidine | 200–201 |
| 3-hydroxypiperidine | 175–177 |
| cis-3,4-dibenzyloxypyrrolidine | 70–75 |
| 3,5-dipropylpiperidine | 170–176 |
| 3,4-dihydroxypiperidine | 172–175 |
| 1-[N-$\beta$-hydroxyethyl-4-piperidyl]-3-[4-piperidyl]propane | 187–190 |
| 4-benzyloxymethylpiperidine | 129–132 |
| 3-methoxypiperidine | 191–193 |
| 1-octamethyleneimine | 232–233 |
| dimethylamine | 175–177.5 |
| 17% aq. ammonia | 209–212 |
| 3-benzylpiperidine | 145–148 |
| 3,5-dibenzylpiperidine | 175–179 |
| 3,4-dichloropiperidine | 185.5–187 |
| 1,2,3,4-tetrahydroisoquinoline | 188–190 |

EXAMPLE 7

2-Bromo-5-(2-methylpiperidinosulfonyl)benzoic Acid

2-Bromo-5-chlorosulfonylbenzoic acid is prepared by reacting o-bromobenzoic acid with chlorosulfonic acid by the method of Example 1. This is reacted with 2-methylpiperidine by the procedure of Example 6. Recrystallization from acetone-hexane yields the product, m.p. 148°–150° C.

Anal. Calc'd for $C_{13}H_{16}O_4NSBr$ (MW 362.2): C, 43.11; H, 4.45; N, 3.87. Found: C, 42.96; H, 4.55; N, 3.74.

EXAMPLE 8

The method of Example 2 is repeated with 2-bromo-5-chlorosulfonylbenzoic acid in place of 2-chloro-5-chlorosulfonylbenzoic acid to yield 2-bromo-5-(trans-dl-3,5-dimethylpiperidinosulfonyl)benzoic acid, m.p. 188°–190° C.

EXAMPLE 9

The following compounds are prepared by reacting 2-bromo-5-chlorosulfonylbenzoic acid with the appropriate amine by the method of Example 7:

| Compound | M.P. (° C.) |
|---|---|
| 2-bromo-5-(cis-3,5-dimethylpiperidinesulfonyl)benzoic acid | 237.5–239.5 |
| 2-bromo-5-(3-trifluoromethyl-4-chlorophenylsulfamyl)benzoic acid | 199–201 |
| 2-bromo-5-(3-phenylpropylsulfamyl)benzoic acid | 160–161 |
| 2-bromo-5-(4-m-tolyl-1-piperazinylsulfonyl)benzoic acid | 207–208 |
| 2-bromo-5-(2-carboxyphenylsulfamyl)benzoic acid | 236–237 |

-continued

| Compound | M.P. (° C.) |
| --- | --- |
| 2-bromo-5-(N-phenyl-N-butylsulfamyl)benzoic acid | 149–151 |
| 2-bromo-5-(4-methoxybenzyl)sulfamylbenzoic acid | 176–176.5 |
| 2-bromo-5-(4-phenylpiperidinosulfonyl)benzoic acid | 193.5–194.5 |
| 2-bromo-5-(3-azabicyclo[3,2,2]nonan-3-ylsulfonyl)benzoic acid | 194.5–195.5 |
| 2-bromo-5-(1,2,5,6-tetrahydro-1-pyridylsulfonyl)benzoic acid | 195–197 |
| 2-bromo-5-(1-methyl-3-hydroxypropylsulfamyl)benzoic acid | 121–123 |
| 2-bromo-5-(3-hydroxymethylpiperidinosulfonyl)benzoic acid | 181–183 |
| 2-bromo-5-(2-carboxy-5-chlorophenylsulfamyl)benzoic acid | 231.5–232 |
| 2-bromo-5-(N-methyl-N-cyclopentylsulfamyl)benzoic acid | 141–143 |
| 2-bromo-5-(3,5-dimethyl-1-piperazinylsulfonyl)benzoic acid | 298–300 |
| 2-bromo-5-(cyclohexylmethylsulfamyl)benzoic acid | 200–202 |
| 2-bromo-5-(1-hexamethyleneiminosulfonyl)benzoic acid | 192–193 |
| 2-bromo-5-(1-heptamethyleneiminosulfonyl)benzoic acid | 216–217.5 |
| 2-bromo-5-(4,4-dimethylpiperidinosulfonyl)benzoic acid | 179–180 |
| 2-bromo-5-octamethyleneiminosulfonylbenzoic acid | 231–232 |
| 2-bromo-5-cyclooctylsulfamylbenzoic acid | 171–173 |
| 2-bromo-5-(3-hydroxypiperidinosulfonyl)benzoic acid | 194–196 |
| 2-bromo-5-(1-pyrrolidinylsulfonyl)benzoic acid | 213–214.5 |
| 2-bromo-5-dimethylaminosulfonyl benzoic acid | 173–174 |
| 2-bromo-5-diethylaminosulfonyl benzoic acid | 143–143.5 |
| 2-bromo-5-cyclopentylsulfamyl benzoic acid | 176–177 |
| 2-bromo-5-sulfamylbenzoic acid | 226–228 |
| 2-bromo-5-(3,5-diethylpiperidinosulfonyl)benzoic acid | 186–188 |
| 2-bromo-5-(3-benzylpiperidinosulfonyl)benzoic acid | 150–154 |
| 2-bromo-5-(3,5-dibenzylpiperidinosulfonyl)benzoic acid | 180–185 |
| 2-bromo-5-(2-[p-chlorophenyl]ethylaminosulfonyl)benzoic acid | 184–185 |

EXAMPLE 10

2-Bromo-5-(N-propyl-N-2-[p-chlorophenyl]ethylaminosulfonylbenzoic acid

2-Bromo-5-(2-[p-chlorophenyl]ethylaminosulfonyl)benzoic acid, 4.2 grams (10 m moles), is combined with 1-iodopropane, 3.4 grams (20 m moles) in 20 ml. 1N aqueous sodium hydroxide and 30 ml. ethanol. This mixture is heated at reflux temperature for 8 hours, with addition of two further 20 m mole portions of iodopropane during the reflux period. Each time iodopropane is added, sufficient sodium hydroxide pellets to keep the reaction mixture basic are also introduced.

The reaction mixture is then evaporated at reduced pressure to remove the ethanol, diluted with water, and washed twice with diethyl ether. The reaction mixture is then acidified with concentrated hydrochloric acid and the oil which separates is extracted three times with diethyl ether. The combined extract is dried, concentrated, treated with hexane and filtered to recover 3.7 grams of solid product.

The product is purified by recrystallization from isopropyl etherhexane and chromatography in benzene on 100 ml. of silica gel in a column. The column is eluted with 5% acetic acid in 1:1 benzene:hexane and the effluent evaporated at reduced pressure to obtain 2.7 grams, m.p. 125°–128° C. Recrystallization from diethyl ether replaced with hexane raises the melting point to 128°–129° C.

Anal. Calc'd for $C_{18}H_{19}O_4NSBrCl$ (MW 461): C, 46.92; H, 4.16; N, 3.04. Found: C, 47.11; H, 4.13; N, 2.88.

EXAMPLE 11

2-Bromo-5-(N-methyl-N-2-[p-chlorophenyl]ethylaminosulfonyl)benzoic Acid

This product is prepared by the procedure of the previous example, substituting 15 m moles of dimethyl sulfate for the iodopropane and employing 40 ml. 1N aqueous sodium hydroxide as reaction medium, with no ethanol.

3.3 Grams of white crystalline product, m.p. 122°–123° C. is obtained.

Anal. Calc'd for $C_{16}H_{15}O_4NSBrCl$: C, 44.40; H, 3.49; N, 3.24. Found: C, 44.11; H, 3.42; N, 3.18.

EXAMPLE 12

2-Bromo-5-(N-benzyl-N-2-[p-chlorophenyl]ethylaminosulfonyl)benzoic Acid

This product is prepared by the procedure of Example 10, substituting 20 m moles of α-bromotoluene for iodopropane. 2.1 Grams of product, m.p. 142°–144° C., is recovered.

Anal. Calc'd for $C_{22}H_{19}O_4NClBr$ (MW 508): C, 51.94; H, 3.76; N, 2.75. Found: C, 52.08; H, 3.87; N, 2.76.

EXAMPLE 13

1-Acetyl-3-hydroxypiperidine

3-Hydroxypiperidine (0.4 mole) is dissolved in 150 ml. of methylene chloride. The solution is cooled to 10° C. and acetic anhydride (0.46 mole) is added dropwise, maintaining the temperature under 20° C. The reaction mixture is allowed to come to room temperature, and is then refluxed for 2 hours. The methylene chloride is evaporated off, and the remaining liquid is distilled under high vacuum. A thick yellow oil is collected at 122°–126° C. (0.3 mm Hg).

1-Acetyl-3-benzyloxypiperidine

1-Acetyl-3-hydroxypiperidine (0.10 mole) is dissolved in 50 ml. of dimethylformamide. 0.12 Mole of sodium hydride (56%) is added over a 10 minute period, and the reaction mixture is stirred for 30 minutes. Benzyl chloride (0.12 mole) is added dropwise over a 30 minute period, and the reaction mixture is then heated on a steam bath for 30 minutes. Water (3 volumes) is added, the solution extracted with ether, the ether extract washed with water and the ether removed by evaporation. A yellow oil is obtained on distillation at 136°–140° C. (0.01 mm Hg.).

Anal. Calc'd for $C_{14}H_{19}O_2N$: C, 72.07; H, 8.21; N, 6.00. Found: C, 72.18; H, 8.25; N, 5.98.

3-Benzyloxypiperidine

1-Acetyl-3-benzyloxypiperidine (0.043 mole), sodium hydroxide (0.086 mole) and water (30 ml.) are combined and refluxed for 24 hours. The reaction mixture is saturated with potassium carbonate and extracted three times with ether. The ether is removed by evaporation and the yellow oil is distilled at 92°–94° C. (0.3 mm Hg.).

2-Bromo-5-(3-benzyloxypiperidinosulfonyl)benzoic Acid

2-Bromo-5-chlorosulfonylbenzoic acid is reacted with 3-benzyloxypiperidine by the method of Example 1. Recrystallization from ether-hexane yields the product, m.p. 177°–178° C.

Anal. Calc'd for $C_{19}H_{20}O_5NSBr$ (MW 454): C, 50.22; H, 4.44; N, 3.08. Found: C, 50.51; H, 4.52; N, 3.41.

2-Chloro-5-(3-benzyloxypiperidinosulfonyl)benzoic Acid

2-Chloro-5-chlorosulfonylbenzoic acid is reacted with 3-benzloxypiperdine by the method of Example 1. Recrystallization from ether-hexane yields the product, m.p. 173°–174° C.

Anal. Calc'd for $C_{19}H_{20}O_5NSCl$: C, 55.67; H, 4.92; N, 3.42. Found: C, 55.93; H, 5.09; N, 3.41.

EXAMPLE 14

Starting with o-fluorobenzoic acid and following the chlorosulfonation conditions of Example 1, 2-fluoro-5-chlorosulfonylbenzoic acid is prepared. This is reacted with the appropriate amine employing the procedure of Example 1, to provide the following compounds:

2-fluoro-5-(4,4-dimethylpiperidinosulfonyl)benzoic acid; 2-fluoro-5-(4-trifluoromethylpiperidinosulfonyl)-benzoic acid; 2-fluoro-5-(3-phenylpiperidinosulfonyl)-benzoic acid; 2-fluoro-5-(3-hydroxymethyl-piperidinosulfonyl)benzoic acid; 2-fluoro-5-(4-n-propoxypiperidinosulfonyl)benzoic acid; 2-fluoro-5-(3-benzyloxypiperidinosulfonyl)benzoic acid; 2-fluoro-5-(4-bromopiperidinosulfonyl)benzoic acid; 2-fluoro-5-(3,5-bis-trifluoromethylpiperidinosulfonyl)benzoic acid; 2-fluoro-5-(2,6-dimethylpiperidinosulfonyl)benzoic acid; 2-fluoro-5-morpholinosulfonylbenzoic acid; 2-fluoro-5-thiomorpholinosulfonylbenzoic acid; 2-fluoro-5-hexamethyleneiminosulfonylbenzoic acid; 2-fluoro-5-(4-phenyl-1-piperizinosulfonyl)benzoic acid; 2-fluoro-5-phenylaminosulfonylbenzoic acid; 2-fluoro-5-(3,4-dichlorobenzylaminosulfonyl)benzoic acid; 2-fluoro-5-(N-methyl-N-[2-p-chlorophenethyl]aminosulfonyl)benzoic acid; 2-fluoro-5-(N-benzyl-N-[3,5-dimethylbenzyl]aminosulfonyl)benzoic acid; 2-fluoro-5-cyclohexylaminosulfonylbenzoic acid; 2-fluoro-5-(N-ethyl-N-cycloheptylaminosulfonyl)benzoic aicd; and 2-fluoro-5-cyclooctylaminosulfonylbenzoic acid.

EXAMPLE 15

2-N,N-diethylamino-5-(3,5-dimethylpiperidinosulfonyl)benzoic Acid o-Fluorobenzoic acid is reacted with chlorosulfonic acid by the method of Example 1 to form 2-fluoro-5-chlorosulfonylbenzoic acid. This is reacted with 3,5-dimethylpiperidine by the method of Example 1 to form 2-fluoro-5-(3,5-dimethylpiperidinosulfonyl)benzoic acid. This product (0.0015 mole) is heated to 60° C. with diethylamine (10 ml.) and ethanol (3.0 ml.) to form a clear solution, and the reaction mixture is then heated at reflux temperature for 24 hours. The resulting brown solid is filtered off, dissolved in 1N NaOH, washed twice with ether, and the product precipitated by the addition of concentrated HCl. Recrystallization from diethyl ether replaced by isopropyl ether yields the product, m.p. 139.5°–140° C.

Anal. Calc'd for $C_{18}H_{28}O_4N_2S$: C, 58.67; H, 7.66; N, 7.60. Found: C, 58.67; H, 7.70; N, 7.53.

EXAMPLE 16

The following compounds are prepared by the method of Example 15.

| Compound | M.P. (° C.) |
| --- | --- |
| 2-piperidino-5-(3,5-dipropylpiperidinosulfonyl)benzoic acid | 135–137 |
| 2-morpholino-5-(3-benzyloxypiperidinosulfonyl)benzoic acid | 178–178.5 |
| 2-piperidino-5-piperidinosulfonylbenzoic acid | 161–164 |
| 2-piperidino-5-(cis-3,5-dimethylpiperidinosulfonyl)benzoic acid | 172–174 |
| 2-diethylamino-5-diethylaminosulfonylbenzoic acid | 129–131.5 |
| 2-(3,5-dimethylpiperidino)-5-(3,5-dimethylpiperidinosulfonyl)benzoic acid | 181–182 |
| 2-n-butylamino-5-(3,5-dimethylpiperidinosulfonyl)benzoic acid | 207–208 |
| 2-piperidino-5-diethylsulfamylbenzoic acid | 154–155.5 |
| 2-dibutylamino-5-piperidinosulfonylbenzoic acid | 102–104 |
| 2-dimethylamino-5-(3,5-dimethylpiperidinosulfonyl)benzoic acid | 195–196.5 |
| 2-piperidino-5-(1-hexamethyleneiminosulfonyl)benzoic acid | 136–137.5 |
| 2-(4-methylpiperidino)-5-(4-methylpiperidinosulfonyl)-benzoic acid | 145–147 |
| 2-(1-hexamethyleneimino)-5-(3,5-dimethylpiperidinosulfonyl)-benzoic acid | 177–179 |

EXAMPLE 17

2-Amino-5-(3,5-dimethylpiperidinosulfonyl)benzoic Acid

2-Fluoro-5-(3,5-dimethylpiperidinosulfonyl)benzoic acid is combined with 10 ml. of benzylamine and heated at 110° C. for 15 minutes. The reaction mixture is concentrated in vacuo (10 mm Hg.) at 85° C. to a thick oil. After the addition of 75 ml. of water, 2-benzylamino-5-(3,5-dimethylpiperidinosulfonyl)benzoic acid, m.p. 220°–227° C., is precipitated by the addition of concentrated hydrochloric acid.

1.9 Grams is dissolved in 50 ml. of acetic acid, and hydrogenated in the presence of 200 mg. of palladium on carbon on a Parr shaker overnight at 60° C. The filtered solution is concentrated to dryness, taken up in 40 ml. of isopropyl alcohol, and allowed to crystallize from 10 ml. of solution. Recrystallization from isopropyl alcohol yields the product, m.p. 240°–241° C.

Anal. Calc'd for $C_{14}H_{20}O_4N_2S$: C, 53.82; H, 6.45; N, 8.97. Found: C, 53.78; H, 6.78; N, 8.64.

EXAMPLE 18

2-Isopropoxy-5-(3-methylpiperidinosulfonyl)benzoic Acid

2-Fluoro-5-chlorosulfonylbenzoic acid is reacted with 3-methylpiperidine by the method of Example 1, and the resulting 2-fluoro-5-(3-methylpiperidinosulfonyl)benzoic acid (5 millimoles) is heated on a steam bath for 3½ hours in isopropyl alcohol (50 ml.) with 5 millimoles of sodium hydride (56.6% suspension in mineral oil). The reaction mixture is evaporated to dryness, and then dissolved in 50 ml. of water. After washing with ether, the aqueous solution is acidified with concentrated HCl. The acid solution is then extracted with ether, and the ether extract washed with water and evaporated to an oil. The oil crystallizes from isopropyl ether-hexane. Recrystallization from the same solvent mixture affords the product, m.p. 102°–104° C.

Anal. Calc'd for $C_{16}H_{23}O_5NS$ (MW 341.4): C, 56.29; H, 6.79; N, 4.10. Found: C, 56.13; H, 6.65; N, 3.66.

EXAMPLE 19

2-Hydroxy-5-(3-methylpiperidinosulfonyl)benzoic Acid

2-Fluoro-5-(3-methylpiperidinosulfonyl)benzoic acid (5 millimoles) and 25 ml. of 1N aqueous sodium hydroxide are heated overnight on a steam bath. The precipitate obtained on acidification of the alkaline solution is redissolved in 2.5N sodium hydroxide and heating is continued on the steam bath for 3½ hours to complete the reaction. Acidification with concentrated HCl yields the crystalline product, m.p. 189°–190° C., which is purified by recrystallization from acetone-hexane.

Anal. Calc'd for $C_{13}H_{17}O_5NS$ (MW 299.3): C, 52.17; H, 5.73; N, 4.68. Found: C, 52.19; H, 5.75; N, 4.52.

EXAMPLE 20

2-Chloro-5-(2-oxopiperidinosulfonyl)benzoic Acid

δ-Amino-n-valeric acid (0.03 mole) is dissolved in 50 ml. of water and 30 ml. of 1N aqueous sodium hydroxide. To this solution is added 2-chloro-5-chlorosulfonylbenzoic acid (0.03 mole) followed by 25 ml. of 2.5N sodium hydroxide. After stirring at room temperature for about 25 minutes, the solution is acidified with concentrated hydrochloric acid. The precipitated 2-chloro-5-(4-carboxybutylsulfamyl)benzoic acid, on recrystallization from acetone-ethyl acetate, melts at 173°–175° C.

Anal. Calc'd for $C_{13}H_{14}O_6NSCl$ (MW 335.8): C, 42.92; H, 4.20; N, 4.17. Found: C, 43.06; H, 4.23; N, 3.90.

2-Chloro-5-(4-carboxybutyl)sulfamylbenzoic acid (0.5 g.) is refluxed for two hours with 10 ml. of thionyl chloride, and then evaporated to dryness to obtain 2-chloro-5-(4-chloroformylbutylsulfamyl)benzoic acid. 0.4 Gram is stirred at room temperature for about 15 minutes with 10 ml. of acetone and 2 ml. of water. The clear solution is evaporated to dryness. The residue is dissolved in hot methanol, and the 2-oxopiperidinosulfonyl product, m.p. 207.5°–209.0° C., is obtained by addition of ether-hexane.

Anal. Calc'd for $C_{12}H_{12}O_5NSCl$ (MW 317.75): C, 45.36; H, 3.81; N, 4.41. Found: C, 45.30; H, 3.83; N, 4.35.

EXAMPLE 21

2-Chloro-5-(4-hydroxymethylpiperidinosulfonyl)benzoic Acid

2-Chloro-5-chlorosulfonylbenzoic acid (5.0 g.) is added to a solution of 4-piperidyl carbinol (6.9 g.) in 40 ml. of methylene chloride. The solution is refluxed for 2 hours, cooled to room temperature and stirred overnight. The solution is evaporated to dryness, the gummy residue dissolved in 1N sodium hydroxide, and the alkaline solution extracted twice with ether. The aqueous solution is acidified with concentrated hydrochloric acid, and the precipitate recovered by filtration. Recrystallization from ethyl acetate yields crystals, m.p. 184°–187° C.

In the same way, the following products are prepared from the corresponding piperidyl carbinols:

|  | M.P. (° C.) |
|---|---|
| 2-chloro-5-(2-hydroxymethylpiperidinosulfonyl)benzoic acid | 136–138 |
| 2-chloro-5-(3-hydroxymethylpiperidinosulfonyl)benzoic acid | 191–193 |

EXAMPLE 22

2-Chloro-5-(4-chloromethylpiperidinosulfonyl)benzoic Acid

2-Chloro-5-(4-hydroxymethylpiperidinosulfonyl)benzoic acid (5.0 g.) is refluxed overnight with 50 ml. of thionyl chloride. After evaporation to dryness, the residue is dissolved in 70 ml. of acetone, 30 ml. of water added and the mixture is allowed to stand at room temperature for a half hour. The solution is then filtered and concentrated to half volume. On the addition of 20 ml. of water a precipitated oil is obtained which crystallizes on stirring. Recrystallization from acetone-benzene yields the product, m.p. 175°–177° C.

Anal. Calc'd for $C_{13}H_{15}O_4NSCl_2$ (MW 352.23): C, 44.33; H, 4.29; N, 3.98. Found: C, 44.85; H, 4.62; N, 3.82.

In the same way, the following chloromethyl compounds are prepared from the products of the previous example:

|  | M.P. (° C.) |
|---|---|
| 2-chloro-5-(2-chloromethylpiperidinosulfonyl)benzoic acid | 134–136 |
| 2-chloro-5-(3-chloromethylpiperidinosulfonyl)benzoic acid | 190–192 |

EXAMPLE 23

2-Chloro-5-(1,2,5,6-tetrahydropyridylsulfonyl)benzoic Acid

2-Chloro-5-chlorosulfonylbenzoic acid (25.5 g.) is added in small portions over a 5 minute period with cooling to a solution of 1,2,5,6-tetrahydropyridine (25.0 g.) in 200 ml. of water. After stirring at room temperature for a half hour, the reaction mixture is acidified with concentrated hydrochloric acid. The crystalline precipitate is filtered off and dissolved in 75 ml. of methylene chloride and 10 ml. of ether. After concentration to 50 ml., hexane is added to turbidity, affording crystals, m.p. 180°–182° C.

2-Chloro-5-(3,4-dibromopiperidinosulfonyl)benzoic Acid

2-Chloro-5-(1,2,5,6-tetrahydropyridylsulfonyl)benzoic acid (2.0 g.) is dissolved in 25 ml. of hot acetic acid. Bromine (3.0 ml.) is added dropwise while heating the acetic acid solution for 2 hours at 100° C. The solution is taken to dryness in vacuo. The residue is dissolved in 20 ml. of 1N sodium hydroxide and then acidified with concentrated hydrochloric acid. The precipitated gum is dissolved in ether, which is then washed with water. The product crystallizes as the ether is replaced with benzene on a steam bath. Recrystallization from acetone-benzene yields the purified product, m.p. 176°–178° C.

Anal. Calc'd for $C_{12}H_{12}O_2NSBr_2Cl$ (MW 461.6): C, 31.22; H, 2.62; N, 3.03. Found: C, 31.44; H, 2.64; N, 3.01.

EXAMPLE 24

2-Chloro-5-(3-methoxy-4-hydroxypiperidinosulfonyl)benzoic Acid

2-Chloro-5-(3,4-dihydroxypiperidinosulfonyl)benzoic acid (4.0 g.) is heated for 16 hours at 90° C. with water (15 ml.), NaOH (1.0 g. and dimethyl sulfate (0.5 ml.). Dimethyl sulfate and NaOH are added during the course of the reaction to maintain basicity. After cooling to room temperature, the reaction mixture is washed with ether and the aqueous phase is acidified with concentrated hydrochloric acid and decanted from the precipitated gum. The gum is dissolved in ethyl acetate and chromatographed on a silica gel column. The product fractions in the column effluent are identified by paper chromatography, with development in a solvent system of ethyl acetate-acetic acid. Concentration of the column fraction yields the product, m.p. 170°–174° C.

Anal. Calc'd for $C_{13}H_{16}O_6NSCl$ (MW 349.8): C, 44.63; H, 4.61; N, 4.04. Found: C, 44.14; H, 4.66; N, 3.74.

EXAMPLE 25

2-Chloro-5-(4-methylenepiperidinosulfonyl)benzoic Acid

2-Chloro-5-(4-chloromethylpiperidinosulfonyl)benzoic acid (0.5 g.) is dissolved in 10 ml. of 5N sodium hydroxide and refluxed for one hour. 10 ml. of water is then added and the mixture is acidified with concentrated hydrochloric acid. The precipitated solid is chromatographed on a 10 g. silica gel column with a developing solvent system of 1:7 benzene:hexane containing 5% acetic acid. 2-Chloro-5-(4-methylenepiperidinosulfonyl)benzoic acid, m.p. 157°–160° C., is isolated from the first fraction.

Anal. Calc'd for $C_{13}H_{14}O_4NSCl$ (MW 316): C, 49.44; H, 4.47; N, 4.44. Found: C, 49.71; H, 4.44; N, 4.28.

In the same way, the following compounds are prepared from the corresponding 5-chloromethylpiperidinosulfonyl benzoic acids:

| | M.P. (° C.) |
|---|---|
| 2-chloro-5-(3-methylenepiperidinosulfonyl)benzoic acid | 165–171 |
| 2-bromo-5-(3-methylenepiperidinosulfonyl)benzoic acid | 158–163 |

EXAMPLE 26

2-Bromo-5-thiomorpholinosulfonylbenzoic Acid

This product is prepared by the reaction of 2-bromo-5-chlorosulfonyl benzoic acid with excess thiomorpholine in methylene chloride. The product, m.p. 195°–197.5° C., is purified by solution in aqueous sodium hydroxide, crystallization by acidifying the basic solution, and recrystallization from acetone-hexane.

Anal. Calc'd for $C_{11}H_{12}O_4NS_2Br$ (MW 366.26): C, 36.07; H, 3.30; N, 3.82. Found: C, 36.24; H, 3.49; N, 3.96.

2-Bromo-5-thiomorphohlinosulfonylbenzoic Acid, 1'-Oxide

The previous product, 1.8 grams (5 m moles) is oxidized by treatment with 0.55 ml. (5.5 m moles) 30% hydrogen peroxide in 20 ml. acetic acid. The reaction mixture is heated on the steam bath 40 minutes and cooled. The resulting crystalline product, 1.5 grams, m.p. 237°–239° C., is recovered by filtration, washed with acetic acid and methanol.

Anal. Calc'd for $C_{11}H_{12}O_5NS_2Br$ (MW 382.26): C, 34.56; H, 3.16; N, 3.66. Found: C, 34.59; H, 3.20; N, 3.46.

EXAMPLE 27

2-Chloro-5-(3,5-dimethylpiperidinosulfonyl)benzoyl chloride

2-Chloro-5-(3,5-dimethylpiperidinosulfonyl)benzoic acid (6.0 g.) is refluxed for 2½ hours with 50 ml. of thionyl chloride, and then taken to dryness. The residue is triturated with 200 ml. of hot benzene-hexane (1:1), filtered and evaporated to obtain the dry product, m.p. 164°–166.5° C.

N-[2-chloro-5-(cis-3,5-dimethylpiperidinosulfonyl)benzoyl]glycine

2-Chloro-5-(cis-3,5-dimethylpiperidinosulfonyl)benzoyl chloride (2.4 g.) and glycine (525 mg.) are dissolved in 30 ml. of water, 30 ml. of acetone and 14 ml. of 1N sodium hydroxide. After stirring at room temperature for about 25 minutes, the reaction mixture is acidified with concentrated hydrochloric acid. The precipitated material is recrystallized from acetone (25 ml.)-hexane (40 ml.) to yield the product, m.p. 189.5°–191.5° C.

Anal. Calc'd for $C_{16}H_{21}O_5N_2SCl$ (MW 388.9): C, 49.41; H, 5.44; N, 7.20. Found: C, 49.55; H, 5.43; N, 7.19.

EXAMPLE 28

N-[2-Chloro-5-(cis-3,5-dimethylpiperidinosulfonyl)benzoyl]-4-aminobutyric Acid 2-Chloro-5-(cis-3,5-dimethylpiperidinosulfonyl)benzoyl chloride (1.75 g.) is added to a solution of 4-aminobutyric acid (0.54 g.) in water (30 ml.), acetone (30 ml.) and 1N sodium hydroxide (10 ml.). After stirring at room temperature for a half hour, the acetone is removed by evaporation, and the aqueous solution is acidified with concentrated hydrochloric acid. The precipitate is dissolved in 50 ml. of hot acetone-methanol (1:1) and concentrated to half volume. Hexane is added to crystallize the product, m.p. 193°–195° C.

Anal. Calc'd for $C_{18}H_{25}O_5N_2SCl$ (MW 416.9): C, 51.85; H, 6.04; N, 6.72. Found: C, 51.43; H, 5.86; N, 6.47.

EXAMPLE 29

2-Methylthio-5-di-n-butylaminosulfonylbenzoic Acid

To a solution containing 11.7 g. (0.03 mole) of 2-bromo-5-di-n-butylaminosulfonylbenzoic acid and 3.6 g. (0.066 mole) of sodium methoxide is added through a gas dispersion tube 4.5 g. (0.1 mole) of methylmercaptan, and the reaction mixture heated under nitrogen at 110° C. for 19 hours. The reaction is cooled, diluted with 150 ml. of water and made strongly basic with a 6N sodium hydroxide solution. The reaction is extracted rapidly with ethyl acetate, and the aqueous layer acidified with 12N hydrochloric acid and extracted with ether. Removal of the ether from the separated organic phase provides 10 g. of the crude product, m.p. 119°-125° C. The product is recrystallized from benzene-hexane, 7.6 g., m.p. 131°-132° C.

Anal. Calc'd for $C_{16}H_{25}O_4NS_2$: C, 53.45; H, 7.01; N, 3.90. Found: C, 53.50; H, 7.06; N, 3.87.

Starting with the appropriate reagents and repeating the general procedure above, the following congeners are synthesized: 2-methylthio-5-dimethylaminosulfonylbenzoic acid, m.p. 216°-217° C. and 2-methylthio-5-sulfamylbenzoic acid, m.p. 278°-279° C.

EXAMPLE 30

2-Chloro-5-(N-ethyl-N-[2-p-chlorophenethyl]aminosulfonyl)benzoic Acid a.
2-chloro-5-(2-p-chlorophenethylaminosulfonyl)benzoic acid

To a solution of 45 g. (0.29 mole) of 2-p-chlorophenethylamine in 200 ml. of methylene chloride is added, portionwise over a 15 minute period, 25.5 g. (0.1 mole) of 2-chloro-5-chlorosulfonylbenzoic acid. An additional 150 ml. of solvent is added, and the mixture is allowed to stir overnight at room temperature. The filtered crude product is dissolved in 1N sodium hydroxide, extracted with ether, and the aqueous layer separated and acidified with 12N hydrochloric acid. The resulting product is filtered and dried, 31 g. m.p. 174°-177° C.

Anal. Calc'd for $C_{15}H_{13}O_4NSCl_2$: C, 48.14; H, 3.50; N, 3.72. Found: C, 48.19; H, 3.31; N, 3.42.

b.
2-chloro-5-(N-ethyl-N-[2-p-chlorophenethyl]aminosulfonyl)benzoic Acid To a refluxing solution of 3.74 g. (0.01 mole) of the above intermediate in 30 ml. of ethanol is gradually added over an eight-hour period 3.12 g. (0.02 mole) of ethyl iodide and 20 ml. (0.02 mole) of 1.0N sodium hydroxide. The reaction mixture is allowed to reflux overnight, after which the solvent is removed under reduced pressure and the residual solid dissolved in 1.0N sodium hydroxide. The aqueous basic solution is washed several times with ether, and is then separated, acidified with 12N hydrochloric acid and extracted with ether. The organic phase is separated, dried over sodium sulfate and concentrated in vacuo. The residual oil on trituration with hexane solidifies, 3.6 g., m.p. 128°-130° C. Recrystallization from chloroform-hexane provides the purified product, m.p. 129°-130° C.

Anal. Calc'd for $C_{17}H_{17}NO_4SCl_2$: C, 50.76; H, 4.26; N, 3.48. Found: C, 50.31; H, 4.26; N, 3.48.

Starting with 2-chloro-5-(p-chlorophenethylaminosulfonyl)benzoic acid and the appropriate halide, and repeating the above alkylation procedure, the following analogs are prepared: 2-chloro-5-(N-benzyl-N-[2-p-chlorophenethyl]aminosulfonyl)benzoic acid, m.p. 140°-142° C., 2-chloro-5-(N-methyl-N-[2-p-chlorophenethyl]aminosulfonyl)benzoic acid, m.p. 126°-128° C.; 2-chloro-5-(N-n-propyl-N-[2-p-chlorophenethyl]aminosulfonyl)benzoic acid, m.p. 137°-139° C. and 2-chloro-5-(N-p-phenylbenzyl-N-[2-p-chlorophenethyl]aminosulfonyl)benzoic acid, m.p. 181°-182.5° C.

EXAMPLE 31

2,3-Dichloro-5-(cis-3,5-dimethylpiperidinosulfonyl)benzoic Acid

To 5.3 g. (45.5 m moles) of chlorosulfonic acid is added portionwise over a period of 5 min. 1.0 g. (5.2 m moles) of commercially available 2,3-dichlorobenzoic acid, and the mixture heated to 155° C. for 2 hrs. The reaction is cooled, poured into 100 g. of ice and the precipitated solid filtered, 1.03 g., m.p. 135°-145° C. Sublimation at 163° C. gave 819 mg., m.p. 148°-151° C. of 2,3-dichloro-5-chlorosulfonylbenzoic acid.

To cis-3,5-dimethylpiperidine (374 mg.; 3.3 m moles) in 3 ml. of methylene chloride is added 192 mg. (0.66 m moles) of 2,3-dichloro-5-chlorosulfonylbenzoic acid and the mixture heated to reflux for 1.5 hrs. The solvent is removed under reduced pressure, and the residue is partitioned between 25 ml. of 1N sodium hydroxide solution and diethyl ether. The aqueous layer is separated, acidified with 6N hydrochloric acid and the resulting precipitated product filtered and dried, 230 mg., m.p. 235°-238° C. Recrystallization from acetonitrile gave the purified product, m.p. 244°-245° C.

Anal. Calc'd for $C_{14}H_{17}O_4NSCl_2$: C, 45.91; H, 4.69; N, 3.84. Found: C, 46.13; H, 4.70; N, 3.76.

EXAMPLE 32

The procedure of Example 31 is repeated, starting with 2,3-dichlorobenzoic acid and the requisite amine to provide the following compounds:

2,3-dichloro-5-piperidinosulfonylbenzoic acid, m.p. 193°-194° C.;
2,3-dichloro-5-di-n- butylaminosulfonylbenzoic acid, m.p. 161°-162° C.; and
2,3-dichloro-5-(2-p-chlorophenethylaminosulfonyl)benzoic acid, m.p. 257°-158.5° C.

EXAMPLE 33

2,3-Dichloro-5-(N-ethyl-N-[2-p-chlorophenethyl]aminosulfonyl)benzoic Acid

In a manner similar to that in Example 30b, 2.0 g. (4.9 m moles) of 2,3-dichloro-5-(2-p-chlorophenethylaminosulfonyl)benzoic acid is alkylated with 2.32 g. (15 m moles) of ethyl iodide in 20 ml. of ethanol containing 15 ml. of 1N sodium hydroxide solution. The crude product was recrystallized from chloroform, 1.04 g., m.p. 142°-144° C.

Anal. Calc'd for $C_{17}H_{16}O_4NSCl_3$: C, 46.75; H, 3.66; N, 3.21. Found: C, 46.77; H, 3.61; N, 3.22.

EXAMPLE 34

Starting with the appropriate 2,3-disubstituted benzoic acid and requisite amine, the procedure of Example 31 is repeated, providing the following compounds:

2,3-difluoro-5-(cis-3,5-dimethylpiperidinosulfonyl)benzoic acid; 2,3-difluoro-5-(2-p-chlorophenethylaminosulfonyl)benzoic acid; 2,3-difluoro-5-morpholinosulfonylbenzoic acid; 2,3-dibromo-5-dimethylaminosulfonylbenzoic acid; 2-bromo-3-chloro-5-hexamethyleneiminosulfonylbenzoic acid; 2-chloro-3-bromo-5-di-n-propylaminosulfonylbenzoic acid; 2-chloro-3-bromo-5-(3,4-dichlorobenzylaminosulfonyl)-benzoic acid; 2-methyl-3-fluoro-5-(4-methylpiperidinosulfonyl)benzoic acid; 2-methyl-3-fluoro-5-di-n-propylaminosulfonylbenzoic acid; 2-methyl-3-fluoro-5-(cis-3,5-dimethylpiperidinosulfonyl)benzoic acid; 2-methyl-3-fluoro-5-(2-p-chlorophenethylaminosulfonyl)benzoic acid; 2-chloro-3-methyl-5-(cis-3,5-dimethylpiperidinosulfonyl)benzoic acid; 2-chloro-3-methyl-5-(2-p-chlorophenethylaminosulfonyl)benzoic acid; 2-methyl-3-chloro-5-(cis-3,5-dimethylpiperidinosulfonyl)benzoic acid; 2-methyl-3-chloro-5-(2-p-chlorophenethylaminosulfonyl)benzoic acid; 2-fluoro-3-chloro-5-cis-3,5-dimethylpiperidinosulfonyl)benzoic acid; 2-fluoro-3-chloro-5-diethylaminosulfonylbenzoic acid; 2-fluoro-3-methyl-5-phenylaminosulfonylbenzoic acid; 2-fluoro-3-chloro-5-piperidinosulfonylbenzoic acid; 2-fluoro-3-trifluoromethyl-5-(cis-3,5-dimethylpiperidinosulfonyl)benzoic acid; 2-chloro-3-trifluoromethyl-5-diethylaminosulfonylbenzoic acid; 2-methyl-3-methoxy-5-diethylaminosulfonylbenzoic acid; 2-methyl-3-methoxy-5-piperidinosulfonylbenzoic acid; and 2-methyl-3-methoxy-5-(2-p-tolylethylaminosulfonyl)benzoic acid.

EXAMPLE 35

2,4-Dichloro-5-piperidinosulfonylbenzoic Acid

A stirred suspension of 1.7 g. (0.02 mole) of piperidine and 5.8 g. (0.02 mole) of 2,4-dichloro-5-chlorosulfonylbenzoic acid (Sturm, et al., Ber., 99, 328 (1966) in 70 ml. of water and cooled to 15° C. is treated dropwise with 50 ml. of 1N sodium hydroxide. When the addition is complete, the mixture is allowed to warm to room temperature and remain for 1 hr. The hazy suspension is filtered and the clear filtrate acidified with 12N hydrochloric acid. The precipitated solids are filtered and dried, 7.7 g., m.p. 200°–205° C. A sample is recrystallized from acetonitrile, m.p. 205°–206° C.

Anal. Calc'd for $C_{12}H_{13}O_4NSCl_2$: C, 42.62; H, 3.87; N, 4.14. Found: C, 42.35; H, 3.77; N, 3.98.

EXAMPLE 36

Substitution of the appropriate amine for piperidine in Example 35 results in the synthesis of 2,4-dichloro-5-(cis-3,5-dimethylpiperidinosulfonyl)benzoic acid, m.p. 236°–237° C.;

2,4-dichloro-5-di-n-propylaminosulfonylbenzoic acid, m.p. 161°–162° C.; and 2,4-dichloro-5-(2-p-chlorophenethylaminosulfonyl)benzoic acid, m.p. 192°–194° C.

EXAMPLE 37

2,4-Dichloro-5-(N-ethyl-N-[2-p-chlorophenethyl]aminosulfonyl)benzoic Acid

The procedure of Example 30b is again repeated, starting with 2.5 g. (6 m moles) of 2,4-dichloro-5-(2-p-chlorophenethylaminosulfonyl)benzoic acid and 3.12 g. (0.02 mole) of ethyl iodide to give 1.74 g. of the desired product, m.p. 132°–134° C.

EXAMPLE 38

Starting with the requisite 2,4-disubstituted benzoic acid, chlorosulfonic acid and the appropriate amine, the procedure of Example 31 is repeated yto provide the following congeners:

2,4-dichloro-5-dimethylaminosulfonylbenzoic acid; 2,4-dichloro-5-(4,4-dimethylpiperidinosulfonyl)benzoic acid; 2,4-difluoro-5-(3-p-bromophenylpropylaminosulfonyl)benzoic acid; 2,4-difluoro-5-morpholinosulfonylbenzoic acid; 2-fluoro-4-chloro-5-(3-chlorophenylaminosulfonyl)benzoic acid; 2-fluoro-4-chloro-5-hexamethyleneiminosulfonylbenzoic acid; 2-chloro-4-fluoro-5-(2,4-dimethylpiperidinosulfonyl)benzoic acid; 2-chloro-4-fluoro-5-(2-p-methylphenethylaminosulfonyl)benzoic acid; 2,4-dibromo-5-(cis-3,5-dimethylpiperidinosulfonyl)benzoic acid; 2,4-dibromo-5-diethylaminosulfonylbenzoic acid; 2,4-dibromo-5-phenylaminosulfonylbenzoic acid; 2-bromo-4-chloro-5-(4-methylpiperidinosulfonyl)benzoic acid; 2-bromo-4-chloro-5-hexamethyleneiminosulfonylbenzoic acid; 2-bromo-4-methyl-5-piperidinosulfonylbenzoic acid; 2-bromo-4-methyl-5-(2-p-chlorophenethylaminosulfonyl)benzoic acid; 2-methyl-4-bromo-5-diethylaminosulfonylbenzoic acid; 2-chloro-4-methyl-5-morpholinosulfonylbenzoic acid; 2-chloro-4-methoxy-5-(2-methylpiperidinosulfonyl)benzoic acid; 2-chloro-4-methoxy-5-(2-chloro-4-bromobenzylaminosulfonyl)benzoic acid; 2-bromo-4-methoxy-5-(2-[3,4-dimethylphenethyl]aminosulfonyl)benzoic acid; 2-chloro-4-methoxy-5-(3-[2-methyl-4-chlorophenylpropyl]aminosulfonyl)benzoic acid; 2-fluoro-4-methyl-5-piperidinosulfonylbenzoic acid; 2-fluoro-4-methyl-5-phenylaminosulfonylbenzoic acid; 2-fluoro-4-methoxy-5-hexamethyleneiminosulfonylbenzoic acid; 2,4-dimethyl-5-morpholinosulfonylbenzoic acid; 2,4-dimethyl-5-di-i-propylaminosulfonylbenzoic acid; 2-methyl-4-methoxy-5-di-n-propylaminosulfonylbenzoic acid; 2-methyl-4-methoxy-5-morpholinosulfonylbenzoic acid; 2-methyl-4-methoxy-5-phenylaminosulfonylbenzoic acid; and 2-methyl-4-methoxy-5-hexamethyleneiminosulfonylbenzoic acid.

EXAMPLE 39

2,6-Dichloro-5-piperidinosulfonylbenzoic Acid (a) To a stirred solution of chlorosulfonic acid (10.6 g.; 0.09 mole) is added 1.91 g. (0.01 mole) of commercially available 2,6-dichlorobenzoic acid and the resulting reaction solution heated to 155° C. for 75 min. The solution is cooled, poured into 100 ml. of ice-water and the resulting white precipitate filtered and dried, 1.8 g., m.p. 155°–160° C. Recrystallization from chloroform gave 1.2 g. of 2,6-dichloro-5-chlorosulfonylbenzoic acid, m.p. 170°–171° C.

Anal. Calc'd for $C_7H_3O_4Sl_3S$: C, 29.04; H, 1.04. Found: C, 29,30; H, 1.05.

(b) 2,6-Dichloro-5-chlorosulfonylbenzoic acid (960 mg.; 3.3 m moles) is added portion-wise to 1.95 g. (0.0165 mole) of piperidine in 15 ml. of dry methylene chloride, and the mixture heated to reflux for 1.5 hrs. The solvent and excess amine are removed under reduced pressure and the residue dissolved in 15 ml. of 2N sodium hydroxide. The aqueous base solution is extracted (2 × 50 ml.) with ether and acidified with 6N hydrochloric acid. The precipitated gum is filtered, dried and allowed to crystallize in hexane, 1.1 g., m.p. 145°–150° C. A small sample is recrystallized from acetonitrile, m.p. 142°–145° C.

Anal. Calc'd for $C_{12}H_{13}O_4NSCl_2$: C, 42.62; H, 3.87; N, 4.14. Found: C, 42.56; H, 4.00; N, 4.02.

EXAMPLE 40

Starting with 2,6-dichloro-5-chlorosulfonylbenzoic acid prepared in Example 39a and the appropriate amine, the following analogs are prepared:

2,6-dichloro-5-(cis-3,5-dimethylpiperidinosulfonyl)benzoic acid, m.p. 157°–159° C.;
2,6-dichloro-5-di-n-propylaminosulfonylbenzoic acid, m.p. 137°–138° C.;
2,6-dichloro-5-(2-p-chlorophenethylaminosulfonyl)benzoic acid, m.p. 90°–91° C.

EXAMPLE 41

Starting with 350 mg. of 2,6-dichloro-5-(2-p-chlorophenethylaminosulfonyl)benzoic acid and 1 ml. of ethyl iodide and following the procedure of Example 30b, 2,6-dichloro-5-(N-ethyl-N-[2-p-chlorophenethyl]aminosulfonyl)benzoic acid is prepared, m.p. 138°–139° C.

EXAMPLE 42

The procedure of Example 31 is repeated, starting with the appropriate amine, 2,6-disubstituted benzoic acid and chlorosulfonic acid, to provide the following compounds:

2,6-dichloro-5-morpholinosulfonylbenzoic acid; 2,6-dichloro-5-di-n-butylaminosulfonylbenzoic acid; 2,6-dichloro-5-(4-bromobenzylaminosulfonyl)benzoic acid; 2-fluoro-6-chloro-5-piperidinosulfonylbenzoic acid; 2-fluoro-6-chloro-5-hexamethyleneiminosulfonylbenzoic acid; 2-fluoro-6-chloro-5-dimethylaminosulfonylbenzoic acid; 2,6-difluoro-5-(3,4-dichlorophenylaminosulfonyl)benzoic acid; 2,6-difluoro-5-morpholinosulfonylbenzoic acid; 2,6-difluoro-5-(4,4-dimethylpiperidinosulfonyl)benzoic acid; 2,6-difluoro-5-(3,5-dimethylpiperidinosulfonyl)benzoic acid; 2-methyl-6-chloro-5-diethylaminosulfonylbenzoic acid; 2-methyl-6-chloro-5-piperidinosulfonylbenzoic acid; 2-chloro-6-methyl-5-hexamethyleneiminosulfonylbenzoic acid; 2-chloro-6-methyl-5-(4-tolylaminosulfonyl)benzoic acid; 2-chloro-6-methyl-5-(3-[4-bromophenylpropyl]aminosulfonyl)benzoic acid; 2-methyl-6-bromo-5-piperidinosulfonylbenzoic acid; 2-methyl-6-bromo-5-(4-tolylaminosulfonyl)benzoic acid; 2-bromo-6-methyl-5-piperidinosulfonylbenzoic acid; 2-bromo-6-methyl-5-(4-tolylaminosulfonyl)benzoic acid; 2-chloro-6-bromo-5-di-n-propylaminosulfonylbenzoic acid; 2-chloro-6-bromo-5-morpholinosulfonylbenzoic acid; 2-bromo-6-chloro-5-piperidinosulfonylbenzoic acid; 2,6-dimethyl-5-hexamethyleneiminosulfonylbenzoic acid; 2,6-dimethyl-5-(4-biphenylaminosulfonyl)benzoic acid; 2,6-dimethyl-5-diethylaminosulfonylbenzoic acid; and 2,6-dimethyl-5-(cis-3,5-dimethylpiperidinosulfonyl)benzoic acid.

EXAMPLE 43

4-Chloro-5-di-n-butylsulfamylbenzoic Acid

To a solution of 3.9 g. (0.03 mole) of di-n-butylamine in 15 ml. of methylene chloride is added 2.5 g. (0.01 mole) of 4-chloro-5-chlorosulfonylbenzoic acid (*J. Pharm. Pharmacol.*, 683 (1962), and the resulting reaction mixture allowed to stir at room temperature for 3 hrs. The solvent is removed under reduced pressure and the residue partitioned between 1N sodium hydroxide and diethyl ether. The aqueous phase is separated, acidified with 12N hydrochloric acid and the precipitated solid filtered and dried, 3.0 g., m.p. 93°–96° C. Recrystallization from ether-hexane provides the pure product, 2.5 g., m.p. 94.5°–96.5° C.

Anal. Calc'd for $C_{15}H_{22}O_4NSCl$: C, 51.79; H, 6.38; N, 4.03. Found: C, 51.86; H, 6.37; N, 3.79.

EXAMPLE 44

Starting with the appropriate 4-substituted benzoic acid and requisite amine, the procedure of Example 30 is repeated to provide the following compounds:

4-fluoro-5-dimethylaminosulfonylbenzoic acid; 4-fluoro-5-piperidinosulfonylbenzoic acid; 4-chloro-5-(3,5-dimethylpiperidinosulfonyl)benzoic acid; 4-chloro-5-morpholinosulfonylbenzoic acid; 4-chloro-5-(3-methylpiperidinosulfonyl)benzoic acid; 4-bromo-5-hexamethyleneiminosulfonylbenzoic acid; 4-bromo-5-(4-chlorobenzylaminosulfonyl)benzoic acid; 4-methyl-5-(4,4-dimethylpiperidinosulfonyl)benzoic acid; 4-methyl-5-(3,5-dibromophenylaminosulfonyl)benzoic acid; 4-methyl-5-(3-phenylpropylaminosulfonyl)benzoic acid; 4-methoxy-5-(2,4-dimethylpiperidinosulfonyl)benzoic acid; 4-methoxy-5-(4-biphenylethylaminosulfonyl)benzoic acid; 4-methoxy-5-(2-p-bromophenethylaminosulfonyl)benzoic acid; and 4-methoxy-5-di-i-propylaminosulfonylbenzoic acid.

EXAMPLE 45

3-Chloro-5-(3-methylpiperidinosulfonyl)benzoic acid

The procedure of Example 43 is repeated, starting with 5 g. (0.05 mole) of 3-methylpiperidine and 2.5 g. (0.01 mole) of 3-chloro-5-chlorosulfonylbenzoic acid in 15 ml. of methylene chloride, providing 2.7 g., m.p. 177°–179° C. of the crude product. Purification is effected by recrystallization from acetone-hexane, 1.2 g., m.p. 181°–183° C.

Anal. Calc'd for $C_{13}H_{16}O_4NSCl$: C, 49.13; H, 5.08; N, 4.41. Found: C, 49.42; H, 5.13; N, 4.35.

EXAMPLE 46

3-Chloro-5-(3,5-dimethylpiperidinosulfonyl)benzoic Acid

3-Chloro-5-chlorosulfonylbenzoic acid (770 mg., 3 m moles) is added to a solution of 3,5-dimethylpiperidine hydrochloride in 30 ml. of water followed by the portionwise addition of 12 ml. of 1N sodium hydroxide solution with stirring. After 1.5 hrs. at room temperature the reaction mixture is filtered and the filtrate acidified with 12N hydrochloric acid. The product, 600 mg., m.p. 226°–331° C., is recrystallized from acetone-hexane, 390 mg., m.p. 232.5°–234° C.

Anal. Calc'd for $C_{14}H_{18}O_4NSCl$: C, 50.67; H, 5.47; N, 4.22. Found: C, 50.43; H, 5.40; N, 4.07.

EXAMPLE 47

3-Trifluoromethyl-5-(3-methylpiperidinosulfonyl)benzoic Acid

The procedure of Example 43 is repeated, starting with 2 g. (0.02 mole) of 3-methylpiperidine in 10 ml. of methylene chloride and 1.8 g. (6.3 m moles) of 3-trifluoromethyl-5-chlorosulfonylbenzoic acid to give, after recrystallization from acetone-hexane, 1.3 g., m.p. 206°–207° C. of the desired product.

Anal. Calc'd for $C_{14}H_{16}O_4NSF_3$: C, 47.86; H, 4.59; N, 3.99. Found: C, 47.82; H, 4.59; N, 3.70.

EXAMPLE 48

Reaction of the appropriately 3-substituted-5-chlorosulfonylbenzoic acid, prepared by chlorosulfonation of the corresponding benzoic acid, with the requisite amine employing the procedure of Example 43 leads to the preparation of the following compounds:

3-fluoro-5-hexamethyleneiminosulfonylbenzoic acid; 3-fluoro-5-di-i-butylaminosulfonylbenzoic acid; 3-fluoro-5-(3,4-dimethylbenzylaminosulfonyl)benzoic acid; 3-bromo-5-morpholinosulfonylbenzoic acid; 3-bromo-5-(3,5-dimethylpiperidinosulfonyl)benzoic acid; 3-bromo-5-diethylaminosulfonylbenzoic acid; 3-methyl-5-piperidinosulfonylbenzoic acid; 3-methyl-5-(4-bromophenylaminosulfonyl)benzoic acid; 3-methyl-5-(2-p-tolylethylaminosulfonyl)benzoic acid; 3-methoxy-5-(2,3-dimethylpiperidinosulfonyl)benzoic acid; 3-methoxy-5-di-i-propylaminosulfonylbenzoic acid; 3-methoxy-5-hexamethyleneiminosulfonylbenzoic acid; 3-chloro-5-(2-p-chlorophenethylaminosulfonyl)benzoic acid; 3-trifluoromethyl-5-(3-p-bromophenylpropylaminosulfonyl)benzoic acid; 3-trifluoromethyl-5-(3,5-dimethylpiperidinosulfonyl)benzoic acid; and 3-trifluoro-5-di-n-butylaminosulfonylbenzoic acid.

EXAMPLE 49

5-(cis-3,5-dimethylpiperidinosulfonyl)-6-chlorobenzoic Acid

To a stirred solution of 95 g. (0.42 mole) of stannous chloride dihydrate in 178 ml. of 12N hydrochloric acid at 50° C. is added dropwise over 30 min. 21.6 g. (0.1 mole) of methyl 2-chloro-3-nitrobenzoate (*J. Chem. Soc.*, 119, 598 (1921). After heating to reflux for 1 hr. the solution is cooled and poured into 1 l. of ice water. Sodium hydroxide solution (500 ml., 40%) is added to adjust the pH above 12 and the mixture is extracted with chloroform (2 × 300 ml.). The organic layer is separated, dried over magnesium sulfate and concentrated to give an oil 11.6 g. A solution of the residual oil in diethyl ether is converted to the hydrochloride salt at 0° C. using hydrogen chloride gas. The intermediate, methyl 3-amino-2-chlorobenzoate hydrochloride is filtered and air dried, 15.9 g., m.p. 188.5°–190° C.

A mixture of 15.6 g. (70 m moles) of 3-amino-2-chlorobenzoate hydrochloride, 70 ml. of acetic acid and 12 ml. of 12N hydrochloric acid is stirred at 10° C. while a solution of sodium nitrite (5.35 g., 77 m moles) in 7 ml. of water is added over a 5 min. period. After stirring at 10° C. for 30 min., sulfur dioxide (42 g., 660 m moles) in 98 ml. of acetic acid containing 704 mg. of cuprous chloride is added, and the green reaction mixture allowed to stir at 10° C. for 1.5 hrs. Water (140 ml.) is then added and the solution is extracted with methylene chloride (3 × 100 ml.). The combined extracts are washed with cold brine solution and dried over magnesium sulfate. Concentration of the organic solution provides 19.6 g. of the crude methyl 2-chloro-3-chlorosulfonylbenzoate.

To a solution of potassium carbonate (24 g., 174 m moles) and cis-3,5-dimethylpiperidine hydrochloride (15.9 g., 105 m moles) in 140 ml. of water is added 18.9 g. of methyl 2-chloro-3-chlorosulfonylbenzoate in 350 ml. of benzene, and the mixture allowed to stir at room temperature for 1 hr. The organic layer is separated, dried over magnesium sulfate and concentrated to an oil which crystallizes on standing. The solid intermediate methyl 5-(cis-3,5-dimethylpiperidinosulfonyl)-6-chlorobenzoate is triturated with hexane and filtered, 19.8 g., m.p. 92.5°–93.5° C.

An aqueous solution of 4.2 g. (105 m moles) of sodium hydroxide in 130 ml. of water is added to 18 g. (52.5 m moles) of methyl 5-(cis-3,5-dimethylpiperidinosulfonyl)-6-chlorobenzoate in 130 ml. of methanol, and resulting reaction mixture allowed to stir at 40° C. for 1 hr. The solution is poured into ice water (1.5 l.) and extracted several times with benzene. The aqueous phase is separated, acidified with 12N hydrochloric acid, and the precipitated product filtered and air dried, 17.3 g. Recrystallization from ethyl acetatehexane gave the purified product, 16.4 g., m.p. 152.5°–153° C.

EXAMPLE 50

The procedure of Example 49 is repeated, starting with the requisite 2-substituted-3-nitrobenzoic acid methyl ester and appropriate amine, to provide the following congeners:

5-morpholinosulfonyl-6-chlorobenzoic acid; 5-diethylaminosulfonyl-6-chlorobenzoic acid; 5-(2-p-chlorophenethylaminosulfonyl)-6-chlorobenzoic acid; 5-hexamethyleneiminosulfonyl-6-fluorobenzoic acid; 5-piperidinosulfonyl-6-fluorobenzoic acid; 5-di-n-propylaminosulfonyl-6-fluorobenzoic acid; 5-(2-p-bromophenethylaminosulfonyl)-6-fluorobenzoic acid; 5-phenylaminosulfonyl-6-bromobenzoic acid; 5-(cis-3,5-dimethylpiperidinosulfonyl)-6-bromobenzoic acid; 5-dimethylaminosulfonyl-6-bromobenzoic acid; 5-hexamethyleneiminosulfonyl-6-bromobenzoic acid; 5-piperidinosulfonyl-6-bromobenzoic acid; 5-(2,4-dimethylpiperidinosulfonyl)-6-methylbenzoic acid; 5-(4,4-dimethylpiperidinosulfonyl)-6-methylbenzoic acid; 5-(2-p-chlorophenethylaminosulfonyl)-6-methylbenzoic acid; 5-(2,3-dichlorobenzylaminosulfonyl)-6-methylbenzoic acid; 5-di-n-butylaminosulfonyl-6-methylbenzoic acid; and 5-morpholinosulfonyl-6-methylbenzoic acid.

EXAMPLE 51

Starting with the appropriate 5-sulfamylbenzoic acid and alkyl iodide and employing the alkylation procedure of Example 30b, the following analogs are synthesized:

2,3-difluoro-5-(N-methyl-N-[2-p-chlorophenethyl]aminosulfonyl)benzoic acid; 2,3-difluoro-5-(N-ethyl-N-[2-p-chlorophenethyl]aminosulfonyl)benzoic acid; 2-chloro-3-bromo-5-(N-n-propyl-N-[3,4-dichlorobenzyl]aminosulfonyl)benzoic acid; 2-methyl-3-fluoro-5-(N-[2-p-chlorophenethyl]aminosulfonyl)benzoic acid; 2-chloro-3-methyl-5-(N-ethyl-N-[2-p-chlorophenethyl]aminosulfonyl)benzoic acid; 2-methyl-3-chloro-5-(N-ethyl-N-[2-p-chlorophenethyl]aminosulfonyl)benzoic acid; 2-fluoro-3-methyl-5-(N-methyl-N-phenylaminosulfonyl)benzoic acid; 2,4-difluoro-5-(N-ethyl-N-[3-p-bromophenylpropyl]aminosulfonyl)benzoic acid; 2-chloro-4-fluoro-5-(N-i-propyl-N-[2-p-tolylethyl]aminosulfonyl)benzoic acid; 2,4-dibromo-5-(N-methyl-N-phenylaminosulfonyl)benzoic acid; 2-bromo-4-methyl-5-(N-n-butyl-N-[2-p-chlorophenethyl]aminosulfonyl)benzoic acid; 2-chloro-4-methoxy-5-(N-methyl-N-[3-{2-methyl-4-chlorophenylpropyl}]aminosulfonyl)benzoic acid; 2-fluoro-4-methyl-5-(N-n-propyl-N-phenylaminosulfonyl)benzoic acid; 2,6-dichloro-5-(N-i-butyl-N-[4-bromobenzyl]aminosulfonyl)benzoic acid; 2,6-difluoro-5-(N-n-butyl-N-[3,4-dichlorophenyl]aminosulfonyl)benzoic acid; 2-chloro-6-methyl-5-(N-ethyl-N-4-tolylaminosulfonyl)benzoic acid; 2-chloro-6-methyl-5-(N-methyl-N-[3-{4-bromophenylpropyl}]aminosulfonyl)benzoic acid; 2-methyl-6-bromo-5-(N-n-propyl-N-4-tolylaminosulfonyl)benzoic acid; 2-bromo-6-methyl-5-(N-ethyl-N-4-tolylaminosulfonyl)benzoic acid; 2,6-dimethyl-5-(N-methyl-N-4-biphenylaminosulfonyl)benzoic acid; 4-bromo-5-(N-methyl-N-[4-bromobenzyl]aminosulfonyl)benzoic acid; 4-methyl-5-(N-i-butyl-N-[3,5-dibromophenyl]aminosulfonyl)benzoic acid; 4-methoxy-5-(N-ethyl-N-4-biphenylaminosulfonyl)benzoic acid; 3-methyl-5-(N-ethyl-N-4-bromophenylaminosulfonyl)benzoic acid; 3-methyl-5-(N-ethyl-N-[2-p-tolylethyl]aminosulfonyl)benzoic acid; 3-chloro-5-(N-ethyl-N-[2-p-chlorophenethyl]aminosulfonyl)benzoic acid; 3-trifluoro-5-(N-methyl-N-[3-p-bromophenylpropyl]aminosulfonyl)benzoic acid; 5-(N-ethyl-N-[2-p-chlorophenethyl]aminosulfonyl)-6-chlorobenzoic acid; 5-(N-i-propyl-N-phenylaminosulfonyl)-6-bromobenzoic acid; 5-(N-ethyl-N-[2-p-chlorophenethyl]aminosulfonyl)-6-methylbenzoic acid; and 2-fluoro-5-(N-methyl-N-phenylaminosulfonyl)benzoic acid.

EXAMPLE 52

The procedure of Example 15 is repeated, starting with the requisite amine and 2-fluoro-5-sulfamylbenzoic acid, to give the following congeners:

2-diethylamino-3-fluoro-5-(cis-3,5-dimethylpiperidinosulfonyl)benzoic acid; 2-piperidino-3-fluoro-5-(cis-3,5-dimethylpiperidinosulfonyl)benzoic acid; 2-piperidino-3-fluoro-5-morpholinosulfonylbenzoic acid; 2-hexamethyleneimino-3-fluoro-5-morpholinosulfonylbenzoic acid; 2-di-n-butylamino-3-chloro-5-(cis-3,5-dimethylpiperidinosulfonyl)benzoic acid; 2-piperidino-3-chloro-5-diethylaminosulfonylbenzoic acid; 2-piperidino-3-methyl-5-phenylaminosulfonylbenzoic acid; 2-hexamethyleneimino-3-chloro-5-piperidinosulfonylbenzoic acid; 2-(N-ethyl-N-n-propylamino)-3-trifluoromethyl-5-(cis-3,5-dimethylpiperidinosulfonyl)benzoic acid; 2-diethylamino-4-fluoro-5-(3-p-bromophenylpropylaminosulfonyl)benzoic acid; 2-piperidino-4-chloro-5-(3-chlorophenylaminosulfonyl)benzoic acid; 2-hexamethyleneimino-4-chloro-5-hexamethyleneiminosulfonylbenzoic acid; 2-di-i-propylamino-4-methyl-5-piperidinosulfonylbenzoic acid; 2-di-n-butylamino-4-methoxy-5-hexamethyleneiminosulfonylbenzoic acid; 2-piperidino-6-fluoro-5-(3,4-dichlorophenylaminosulfonyl)benzoic acid; 2-diethylamino-6-fluoro-5-morpholinosulfonylbenzoic acid; 2-piperidino-6-fluoro-5-(4,4-dimethylpiperidinosulfonyl)benzoic acid; 2-diethylamino-3-fluoro-5-(N-methyl-N-[2-p-chlorophenethyl]aminosulfonyl)benzoic acid; 2-piperidino-3-fluoro-5-(N-ethyl-N-[2-p-chlorophenethyl]aminosulfonyl)benzoic acid; 2-hexamethyleneimino-3-methyl-5-(N-methyl-N-phenylaminosulfonyl)benzoic acid; 2-di-n-propylamino-6-fluoro-5-(N-n-butyl-N-[3,4-dichlorophenyl]aminosulfonyl)benzoic acid; and 2-piperidino-6-fluoro-5-(N-n-butyl-N-[3,4-dichlorophenyl]aminosulfonyl)benzoic acid.

EXAMPLE 53

The procedure of Example 18 is repeated, starting with the appropriate 2-fluoro-5-sulfamylbenzoic acids and methanol in place of isopropanol, to give the following compounds:

2-methoxy-3-fluoro-5-(cis-3,5-dimethylpiperidinosulfonyl)benzoic acid; 2-methoxy-3-fluoro-5-morpholinosulfonylbenzoic acid; 2-methoxy-3-chloro-5-(cis-3,5-dimethylpiperidinosulfonyl)benzoic acid; 2-methoxy-3-chloro-5-diethylaminosulfonylbenzoic acid; 2-methoxy-3-methyl-5-phenylaminosulfonylbenzoic acid; 2-methoxy-3-chloro-5-piperidinosulfonylbenzoic acid; 2-methoxy-3-trifluoromethyl-5-(cis-3,5-dimethylpiperidinosulfonyl)benzoic acid; 2-methoxy-4-fluoro-5-(3-p-bromophenylpropylaminosulfonyl)benzoic acid; 2-methoxy-4-fluoro-5-morpholinosulfonylbenzoic acid; 2-methoxy-4-chloro-5-hexamethyleneiminosulfonylbenzoic acid; 2-methoxy-4-methyl-5-piperidinosulfonylbenzoic acid; 2-methoxy-4-methyl-5-phenylaminosulfonylbenzoic acid; 2,4-dimethoxy-5-hexamethyleneiminosulfonylbenzoic acid; 2-methoxy-6-fluoro-5-(3,4-dichlorophenylaminosulfonyl)benzoic acid; 2-methoxy-3-fluoro-5-(N-ethyl-N-[2-p-chlorophenethyl]aminosulfonyl)benzoic acid; 2-methoxy-3-methyl-5-(N-methyl-N-phenylaminosulfonyl)benzoic acid; and 2-methoxy-4-methyl-5-(N-n-propyl-N-phenylaminosulfonyl)benzoic acid.

EXAMPLE 54

A dry solid pharmaceutical composition is prepared by blending the following materials together in the specified weight proportions:

| | |
|---|---|
| 2-chloro-5-(cis-3,5-dimethylpiperidinosulfonyl)benzoic acid | 50 |
| sodium citrate | 25 |
| alginic acid | 10 |
| polyvinylpyrrolidone | 10 |
| magnesium stearate | 5 |

After the dried composition is thoroughly blended, tablets are punched from the mixture, each tablet being of such size as to contain 100 mg. of the active ingredient. Tablets are also prepared containing, respectively, 5, 10, 25 and 50 mg. of the active ingredient, by employing the appropriate proportions of 2-chloro-5-(cis-3,5-dimethylpiperidinosulfonyl)benzoic acid and excipient blend in each case.

EXAMPLE 55

A dry solid pharmaceutical composition is prepared by combining the following materials in the indicated weight proportions:

| | |
|---|---|
| 2-chloro-5-(cis-3,5-dimethylpiperidinosulfonyl)benzoic acid | 50 |
| calcium carbonate | 20 |
| polyethylene glycol, average molecular weight 4000 | 30 |

The dry mixture is thoroughly agitated to obtain a completely uniform blend. Soft elastic and hard gelatin capsules containing this composition are then prepared, employing sufficient material to provide each capsule with 190 mg. of active ingredient.

EXAMPLE 56

Groups, each comprising 4 animals, of normal Sprague-Dawley (Charles River) male rats weighing from 160 to 220 grams are fed rat chow containing the test compounds for two overnight feeding periods. On the morning of the third day the animals are anesthetized and bled from the abdominal aorta. The total plasma cholesterol is then determined by the method of J. J. Carr and I. J. Drekter reported in *Clin. Chem.*, 2, 353 (1956). Most of the tests are conducted at a concentration in the feed of 0.15 to 0.25 weight percent of the compound under test, but lower levels are employed in some instances. The total quantity of test compound consumed is computed from feed consumption over the two-day period and is tabulated, in milligrams per kilogram body weight per day, along with the associated percent cholesterol fall measured:

| Compound | % Cholesterol Fall | Daily Dosage mg./kg. |
| --- | --- | --- |
| 2-chloro-5-(trans-dl-3,5-dimethylpiperidinosulfonyl)benzoic acid | 35 | 126 |
| 2-chloro-5-(cis-3,5-dimethylpiperidinosulfonyl)benzoic acid | 44 | 112 |
| 2-chloro-4-(cis-3,5-dimethylpiperidinosulfonyl)benzoic acid | inactive | 182 |
| 2-bromo-5-(cis-3,5-dimethylpiperidinosulfonyl)benzoic acid | 40 | 120 |
| 2-bromo-5-(3-benzyloxypiperidinosulfonyl)benzoic acid | 25 | 114 |
| 2-chloro-5-(3-benzyloxypiperidinosulfonyl)benzoic acid | 26 | 129 |
| 2-chloro-5-(2,5-dimethylpiperidinosulfonyl)benzoic acid | 35 | 110 |
| 2-bromo-5-(3-trifluoromethyl-4-chlorophenylsulfamyl)benzoic acid | 38 | 174 |
| 2-chloro-5-(3,5-dimethylmorpholinosulfonyl)benzoic acid | 29 | 156 |
| 2-isopropoxy-5-(3-methylpiperidinosulfonyl)benzoic acid | 22 | 149 |
| 2-hydroxy-5-(3-methylpiperidinosulfonyl)benzoic acid | 35 | 134 |
| 2-piperidino-5-(piperidinosulfonyl)benzoic acid | 35 | 129 |
| 2-bromo-5-(1-methyl-3-hydroxypropylsulfamyl)benzoic acid | 16 | 279 |
| 2-bromo-5-(3-phenylpropylaminosulfonyl)benzoic acid | 26 | 131 |
| 2-bromo-5-(4-m-tolyl-1-piperazinylsulfonyl)benzoic acid | 20 | 123 |
| 2-bromo-5-(2-carboxyphenylsulfamyl)benzoic acid | 37 | 273 |
| 2-chloro-5-(2-oxopiperidinosulfonyl)benzoic acid | 30 | 136 |
| 2-pyrrolidinyl-5-(3,5-dimethylpiperidinosulfonyl)benzoic acid | 31 | 215 |
| N-[2-chloro-5-(cis-3,5-dimethylpiperidinosulfonyl)benzoyl]glycine | 35 | 180 |
| N-[2-chloro-5-(cis-3,5-dimethylpiperidinosulfonyl)benzoyl]-4-aminobutyric acid | 44 | 129 |
| 2-amino-5-(cis-3,5-dimethylpiperidinosulfonyl)benzoic acid | 26 | 143 |
| 2-bromo-5-(3-hydroxymethylpiperidinosulfonyl)benzoic acid | 20 | 23 |
| 2-morpholino-5-(3-benzyloxypiperidinosulfonyl)benzoic acid | 29 | 139 |
| 2-chloro-5-(3,5-dipropylpiperidinosulfonyl)benzoic acid | 39 | 47 |
| 2-diethylamino-5-(diethylaminosulfonyl)benzoic acid | 21 | 44 |
| 2-bromo-5-[2-(p-chlorophenyl)ethylaminosulfonyl]-benzoic acid | 21 | 22 |
| 2-bromo-5-(N-phenyl-N-butylsulfamyl)benzoic acid | 17 | 236 |
| 2-bromo-5-(4-methoxybenzylsulfamyl)benzoic acid | 20 | 363 |
| 2-bromo-5-(4-phenylpiperidinosulfonyl)benzoic acid | 28 | 226 |
| 2-bromo-5-(3-azabicyclo[3,2,2]nonan-3-ylsulfonyl)benzoic acid | 32 | 228 |
| 2-bromo-5-(1,2,5,6-tetrahydro-1-pyridylsulfonyl)benzoic acid | 22 | 149 |
| 2-chloro-5-(2,2-dimethylthiomorpholinosulfonyl)benzoic acid | 35 | 139 |
| 2-chloro-5-(2-benzylpiperidinosulfonyl)benzoic acid | 32 | 124 |
| 2-chloro-5-(4-phenyl-4-ethoxypiperidinosulfonyl)benzoic acid | 13 | 136 |
| 2-chloro-5-(3-hydroxypiperidinosulfonyl)benzoic acid | 23 | 135 |
| 2-chloro-5-(3,4-dibromopiperidinosulfonyl)benzoic acid | 21 | 46 |
| 2-chloro-5-(cis-3,4-dibenzyloxy-1-pyrrolidinylsulfonyl)benzoic acid | 25 | 126 |
| 2-chloro-5-(3-methoxy-4-hydroxypiperidinosulfonyl)benzoic acid | 15 | 141 |
| 2-bromo-5-(thiomorpholinosulfonyl)benzoic acid, 1'-oxide | 20 | 270 |
| 2-bromo-5-cyclooctylsulfamylbenzoic acid | 25 | 181 |
| 2-bromo-5-cyclohexylmethylsulfamylbenzoic acid | 27 | 126 |
| 2-chloro-5-(3,5-dibenzylpiperidinosulfonyl)benzoic acid | 24 | 131 |
| 2-bromo-5-(3,5-dibenzylpiperidinosulfonyl)benzoic acid | 38 | 118 |
| 2-bromo-5-(3-hydroxypiperidinosulfonyl)benzoic acid | 26 | 126 |
| 2-(4-methylpiperidino)-5-(4-methylpiperidinosulfonyl)benzoic acid | 35 | 140 |
| 2-chloro-5-(3-methoxypiperidinosulfonyl)benzoic acid | 20 | 152 |
| 2-(1-hexamethyleneimino)-5-(3,5-di-methylpiperidinosulfonyl)benzoic acid | 14 | 45 |
| 2-bromo-5-(1-hexamethyleneiminosulfonyl)benzoic acid | 28 | 212 |
| 2-bromo-5-(1-heptamethyleneiminosulfonyl)benzoic acid | 23 | 218 |
| 2-chloro-5-(1-octamethyleneiminosulfonyl)benzoic acid | 31 | 133 |
| 2-piperidino-5-(1-heptamethyleneiminosulfonyl)benzoic acid | 20 | 24 |
| 2-piperidino-5-(1-hexamethyleneiminosulfonyl)benzoic acid | 23 | 44 |
| 2-chloro-5-(2-[p-chlorophenyl]ethylaminosulfonyl)benzoic acid | 30 | 49 |
| 2-diethylamino-5-(3,5-dimethylpiperidinosulfonyl)benzoic acid | 41 | 77 |

-continued

| Compound | % Cholesterol Fall | Daily Dosage mg./kg. |
|---|---|---|
| 2-n-butylamino-5-(3,5-dimethylpiperidinosulfonyl)-benzoic acid | 14 | 130 |
| 2-di-n-butylamino-5-(3,5-dimethylpiperidinosulfonyl)-benzoic acid | 22 | 9 |
| 2-piperidino-5-diethylaminosulfonylbenzoic acid | 22 | 47 |
| 2-(3,5-dimethylpiperidino)-5-(piperidinosulfonyl)-benzoic acid | 21 | 49 |
| 2-(3,5-dimethylpiperidino)-5-dibutylsulfamylbenzoic acid | 12 | 22 |
| 2-chloro-5-(4-chloromethylpiperidinosulfonyl)benzoic acid | 21 | 127 |
| 2-chloro-5-(4-benzyloxymethylpiperidinosulfonyl)-benzoic acid | 23 | 20 |
| 2-chloro-5-(4-chloropiperidinosulfonyl)benzoic acid | 16 | 48 |
| 2-chloro-5-(3,4-dichloropiperidinosulfonyl)benzoic acid | 40 | 104 |
| 2-chloro-5-(3-benzylpiperidinosulfonyl)benzoic acid | 31 | 25 |
| 2-chloro-5-(3-methylenepiperidinosulfonyl)benzoic acid | 30 | 21 |
| 2-bromo-5-(3-hydroxypiperidinosulfonyl)benzoic acid | 26 | 126 |
| 2-bromo-5-(3-benzylpiperidinosulfonyl)benzoic acid | 35 | 23 |
| 2-bromo-5-(3-methylenepiperidinosulfonyl)benzoic acid | 31 | 39 |
| 2-(3-methylpiperidino)-5-(3-methylpiperidinosulfonyl)-benzoic acid | 22 | 136 |
| 2-(cis-3,5-dimethylpiperidino)-5-(cis-3,5-dimethyl-piperidinosulfonyl)benzoic acid | 37 | 195 |
| 2-(3-methylpiperidino)-5-piperidinosulfonylbenzoic acid | 12 | 23 |
| 2-chloro-5-($\beta,\beta'$-dichloro-diethylaminosulfonyl)benzoic acid | 23 | 125 |
| 2-bromo-5-[N-ethyl, N-[2-p-chlorophenylethyl]amino-sulfonyl)benzoic acid | 39 | 32 |
| 2-bromo-5-(N-methyl, N-[2-p-chlorophenylethyl]amino-sulfonyl)benzoic acid | 31 | 21 |
| 2-bromo-5-(N-propyl, N-[2-chlorophenylethyl]amino-sulfonyl)benzoic acid | 34 | 21 |
| 2-bromo-5-(N-isobutyl, N-[2-p-chlorophenylethyl]-aminosulfonyl)benzoic acid | 34 | 22 |
| 2-bromo-5-(N-benzyl, N-[2-p-chlorophenylethyl]amino-sulfonyl)benzoic acid | 34 | 23 |
| 2-bromo-5-(1-pyrrolidinylsulfonyl)benzoic acid | 19 | 169 |
| 2-bromo-5-(diethylaminosulfonyl)benzoic acid | 33 | 267 |
| 2-bromo-5-(dimethylaminosulfonyl)benzoic acid | 10 | 247 |
| 2-chloro-5-(dimethylaminosulfonyl)benzoic acid | 27 | 253 |
| 2-piperidino-5-(3-azabicyclo[3,2,2]nonan-3-ylsul-fonyl)benzoic acid | 35 | 153 |
| 2-bromo-5-(cyclopentylsulfamyl)benzoic acid | 12 | 229 |
| 2-bromo-5-sulfamyl benzoic acid | 10 | 185 |
| 2-chloro-5-sulfamyl benzoic acid | 10 | 265 |
| 2-chloro-5-(3-hydroxymethylpiperidinosulfonyl)benzoic acid | 14 | 131 |
| 2-chloro-5-(3,5-diethylpiperidinosulfonyl)benzoic acid | 42 | 5 |
| 2-bromo-5-(3,5-diethylpiperidinosulfonyl)benzoic acid | 36 | 273 |
| 2-chloro-5-(4-hydroxymethylpiperidinosulfonyl)benzoic acid | 15 | 222 |
| 2-bromo-5-(2-methylpiperidinosulfonyl)benzoic acid | 29 | 72 |
| 2-bromo-5-(2-carboxyl-5-chlorophenylsulfamyl)benzoic acid | 13 | 282 |
| 2-bromo-5-(4,4-dimethylpiperidinosulfonyl)benzoic acid | 30 | 122 |
| 2-bromo-5-(octamethyleneiminosulfonyl)benzoic acid | 37 | 158 |
| 2-piperidino-5-(3,5-dipropylpiperidinosulfonyl)benzoic acid | 18 | 23 |
| 2-piperidino-5-(cis-3,5-dimethylpiperidinosulfonyl)-benzoic acid | 32 | 37 |
| 2-dibutylamino-5-(piperidinosulfonyl)benzoic acid | 14 | 5 |
| 2-dimethylamino-5-(3,5-dimethylpiperidinosulfonyl)-benzoic acid | 11 | 22 |
| 2-chloro-5-(2-hydroxymethylpiperidinosulfonyl)benzoic acid | 14 | 124 |
| 2-chloro-5-(3-hydroxymethylpiperidinosulfonyl)benzoic acid | 14 | 131 |
| 2-chloro-5-(2-chloromethylpiperidinosulfonyl)benzoic acid | 38 | 95 |
| 2-chloro-5-(3-chloromethylpiperidinosulfonyl)benzoic acid | 18 | 5 |
| 2-chloro-5-(4-methylenepiperidinosulfonyl)benzoic acid | 29 | 39 |
| 2-bromo-5-[N-isopropyl-N-2-(p-chlorophenyl)ethyl-aminosulfonyl]benzoic acid | 27 | 24 |
| 2-piperidino-5-[2-(p-chlorophenyl)ethylaminosulfonyl]-benzoic acid | 33 | 251 |
| 2-chloro-5-(3,4-dihydroxypiperidinosulfonyl)benzoic acid | 11 | 225 |
| 2-bromo-5-(N-methyl-N-cyclohexylsulfamyl)benzoic acid | 13 | 226 |
| 2-bromo-5-(3,5-dimethyl-1-piperazinylsulfonyl)benzoic acid | 11 | 226 |
| 3-chloro-5-(3-methylpiperidinosulfonyl)benzoic acid | 24 | 113 |
| 4-chloro-5-di-n-butylaminosulfonylbenzoic acid | 14 | 124 |
| 3-trifluoromethyl-5-(3-methylpiperidinosulfonyl)-benzoic acid | 13 | 144 |
| 4-chloro-2-di-n-butylaminosulfonylbenzoic acid | 13 | 133 |
| 5-methyl-2-benzylaminosulfonylbenzoic acid | 17 | 240 |
| 3-chloro-5-(3,5-dimethylpiperidinosulfonyl)benzoic | 13 | 66 |

-continued

| Compound | % Cholesterol Fall | Daily Dosage mg./kg. |
|---|---|---|
| 5-chloro-2-piperidinosulfonylbenzoic acid | 12 | 117 |
| 5-chloro-2-(3,5-dimethylpiperidinosulfonyl)benzoic acid | 24 | 128 |
| 4-chloro-2-(3,5-dimethylpiperidinosulfonyl)benzoic acid | 39 | 93 |
| 4-chloro-2-(3-methylpiperidinosulfonyl)benzoic acid | 36 | 133 |
| 2-methylthio-5-dimethylaminosulfonylbenzoic acid | 40 | 243 |
| 2-methylthio-5-sulfamylbenzoic acid | 25 | 241 |
| 2-methylthio-5-di-n-butylaminosulfonylbenzoic acid | 38 | 224 |
| 2-chloro-5-(N-benzyl-N-[2-p-chlorophenethyl]aminosulfonylbenzoic acid | 25 | 5 |
| 2-chloro-5-(N-methyl-N-[2-p-chlorophenethyl]aminosulfonyl)benzoic acid | 29 | 22 |
| 2-chloro-5-(N-p-phenylbenzyl-N-[2-p-chlorophenethyl]-aminosulfonyl)benzoic acid | 20 | 20 |
| 2-chloro-5-(1,2,3,4-tetrahydro-2-isoquinolylsulfonyl)-benzoic acid | 38 | 135 |
| 2,6-dichloro-5-(cis-3,5-dimethylpiperidinosulfonyl)-benzoic acid | 22 | 204 |
| 2,6-dichloro-5-(2-p-chlorophenethylaminosulfonyl)-benzoic acid | 14 | 170 |
| 2,6-dichloro-5-(N-ethyl-N-[2-p-chlorophenethyl]aminosulfonyl)benzoic acid | 16 | 183 |
| 6-chloro-5-(cis-3,5-dimethylpiperidinosulfonyl)-benzoic acid | 31 | 76 |
| 2,3-dichloro-5-(cis-3,5-dimethylpiperidinosulfonyl)-benzoic acid | 27 | 42 |
| 2,3-dichloro-5-piperidinosulfonylbenzoic acid | 23 | 85 |
| 2,3-dichloro-5-di-n-propylaminosulfonylbenzoic acid | 28 | 140 |
| 2,3-dichloro-5-(N-ethyl-N-[2-p-chlorophenethyl]aminosulfonyl)benzoic acid | 26 | 168 |
| 2,4-dichloro-5-piperidinosulfonylbenzoic acid | 26 | 200 |
| 2,4-dichloro-5-di-n-propylaminosulfonylbenzoic acid | 19 | 169 |
| 2,4-dichloro-5-(cis-3,5-dimethylpiperidinosulfonyl)-benzoic acid | 19 | 22 |
| 2,4-dichloro-5-(N-ethyl-N-[2-p-chlorophenethyl]-aminosulfonyl)benzoic acid | 12 | 188 |
| 4-di-n-propylaminosulfonylbenzoic acid | inactive | |
| 3-bromo-4-(3-methylpiperidinosulfonyl)benzoic acid | inactive | |
| 2-n-butylaminosulfonylbenzoic acid | inactive | |
| 3-bromo-4-(4-methylpiperidinosulfonyl)benzoic acid | inactive | |
| 3-bromo-4-diethylaminosulfonylbenzoic acid | inactive | |
| 4-(3-methylpiperidinosulfonyl)benzoic acid | inactive | |
| 2-chloro-4-morpholinosulfonylbenzoic acid | inactive | |
| 2-morpholinosulfonyl-5-chlorobenzoic acid | inactive | |
| 2-di-n-butylaminosulfonyl-5-chlorobenzoic acid | inactive | |
| 2-fluoro-5-(3-methylpiperidinosulfonyl)benzoic acid | 24 | 150 |
| 2-fluoro-5-(4,4-dimethylpiperidinosulfonyl)benzoic acid | 25 | 155 |
| 2-fluoro-5-(4-methylpiperidinosulfonyl)benzoic acid | 25 | 149 |
| 2-fluoro-5-piperidinosulfonylbenzoic acid | 31 | 150 |
| 2-fluoro-5-diethylaminosulfonylbenzoic acid | 31 | 146 |
| 2-fluoro-5-(3,5-dimethylpiperidinosulfonyl)benzoic acid | 22 | 123 |
| 2-fluoro-5-(3-benzyloxypiperidinosulfonyl)benzoic acid | 22 | 135 |
| 2-fluoro-5-(4-benzylpiperidinosulfonyl)benzoic acid | 19 | 138 |
| 2-fluoro-5-(2-benzylpiperidinosulfonyl)benzoic acid | 22 | 76 |
| 2-fluoro-5-(4-benzyloxypiperidinosulfonyl)benzoic acid | 18 | 135 |
| 2-fluoro-5-di-n-butylaminosulfonylbenzoic acid | 19 | 210 |
| 2-fluoro-5-(2-p-chlorophenethylaminosulfonyl)benzoic acid | 23 | 120 |
| 2-fluoro-5-hexamethyleneiminosulfonylbenzoic acid | 23 | 119 |
| 2-fluoro-5-(3,5-di-n-propylpiperidinosulfonyl)benzoic acid | 36 | 121 |

What is claimed is:

1. A compound selected from the group consisting of those of the formula

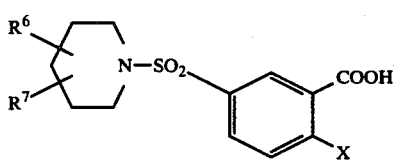

and the amides, lower alkyl esters and salts thereof with pharmacologically acceptable bases, wherein X is selected from the group consisting of piperidino, mono- and di-lower-alkylpiperidino, hexamethyleneimino and morpholino;

$R^6$ is selected from the group consisting of alkyl, alkyloxy and alkyloxyalkyl of one to four carbon atoms in each alkyl group, hydroxy, chloro, bromo, trifluoromethyl, methylene, oxo, phenyl, tolyl, benzyl, benzyloxy, benzyloxymethyl, chloromethyl and hydroxymethyl; and $R^7$ is selected from the group consisting of hydrogen, alkyl, alkyloxy and alkyloxyalkyl of one to four carbon atoms in each alkyl group, hydroxy, chloro, bromo, trifluoromethyl, phenyl, tolyl, benzyl, benzyloxy, benzyloxymethyl, chloromethyl and hydroxymethyl.

2. The compound of claim 1 wherein X is morpholino, $R^6$ is 3-benzyloxy and $R^7$ is hydrogen.

3. The compound of claim 1 wherein X is 4-methylpiperidino, $R^6$ is 4-methyl and $R^7$ is hydrogen.

4. The compound of claim 1 wherein X is 1-hexamethyleneimino, $R^6$ is 3-methyl and $R^7$ is 5-methyl.

5. A compound selected from the group consisting of those of the formula

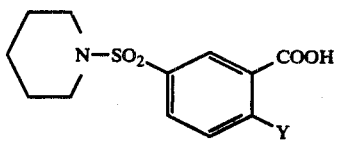

and the amides, lower alkyl esters and salts thereof with pharmacologically acceptable bases, wherein Y is selected from the group consisting of piperidino and mono- and di-lower-alkyl piperidino.

6. The compound of claim 5 wherein Y is piperidino.

7. The compound of claim 5 wherein Y is 3,5-dimethylpiperidino.

8. A compound selected from the group consisting of those of the formula

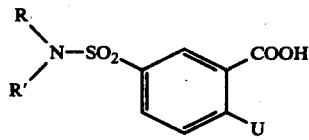

and the amides, lower alkyl esters and salts thereof with pharmacologically acceptable bases, wherein U is selected from the group consisting of piperidino, mono- and di-lower-alkylpiperidino, morpholino, and hexamethyleneimino;

and R and R' together with the nitrogen to which they are attached form a heterocyclic ring selected from the group consisting of morpholino, thiomorpholino, piperazinyl, 3-azabicyclo(3,2,2)nonanyl, tetrahydroisoquinolyl, tetrahydropyridyl and mono- and disubstituted derivatives of said heterocyclic rings;

said substituents being selected from the group consisting of alkyl, alkyloxy and alkyloxyalkyl of one to four carbon atoms in each alkyl group, hydroxy, chloro, bromo, trifluoromethyl, phenyl, tolyl, benzyl, benzyloxy, chloromethyl and hydroxymethyl.

9. The compound of claim 8 wherein U is piperidino and R and R' together with the nitrogen form a 3-azabicyclo[3,2,2]nonan-3-yl ring.

10. A compound selected from the group consisting of those of the formula

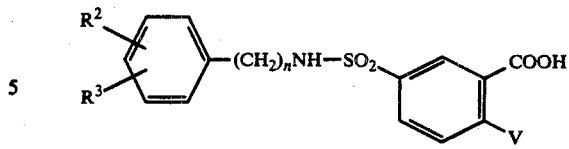

and the amides, lower alkyl esters and salts thereof with pharmacologically acceptable bases, wherein n has a value from 0 to 3;

V is selected from the group consisting of piperidino and mono- and di-lower-alkylpiperidino; and $R^2$ and $R^3$ are each selected from the group consisting of hydrogen, chloro, bromo, alkyl and alkoxy of from one to four carbon atoms, carboxy, trifluoromethyl, phenyl, benzyl and benzyloxy.

11. A compound selected from the group consisting of those of the formula

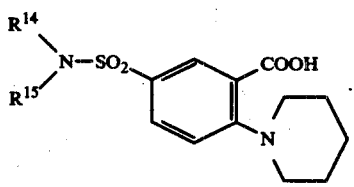

wherein $R^{14}$ and $R^{15}$ are each lower alkyl.

12. The compound of claim 11 wherein $R^{14}$ and $R^{15}$ are each ethyl.

13. A compound selected from the group consisting of those of the formula

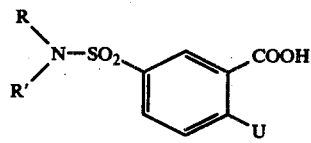

and the amides, lower alkyl esters and salts thereof with pharmacologically acceptable bases, wherein U is selected from the group consisting of di-lower-alkylamino, piperidino, mono- and di-lower-alkylpiperidino, morpholino, and hexamethyleneimino;

and R and R' together with the nitrogen to which they are attached form a heterocyclic ring selected from the group consisting of hexamethyleneimino, heptamethyleneimino and octamethyleneimino, tetrahydropyridyl and mono- and disubstituted derivatives of said heterocyclic rings;

said substituents being selected from the group consisting of alkyl, alkyloxy and alkyloxyalkyl of one to four carbon atoms in each alkyl group, hydroxy, chloro, bromo, trifluoromethyl, phenyl, tolyl, benzyl, benzyloxy, chloromethyl and hydroxymethyl.

14. The compound of claim 13 wherein U is piperidino and R and R' together with the nitrogen form a 1-heptamethyleneimino ring.

* * * * *